(12) United States Patent
Samuels et al.

(10) Patent No.: US 12,292,440 B2
(45) Date of Patent: *May 6, 2025

(54) SANDWICH ASSAYS IN DROPLETS

(71) Applicant: Bio-Rad Laboratories, Inc., Hercules, CA (US)

(72) Inventors: Michael L. Samuels, Windham, NH (US); Darren Roy Link, Lexington, MA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/653,506

(22) Filed: May 2, 2024

(65) Prior Publication Data

US 2024/0280569 A1    Aug. 22, 2024

Related U.S. Application Data

(63) Continuation of application No. 18/305,650, filed on Apr. 24, 2023, which is a continuation of application No. 16/937,908, filed on Jul. 24, 2020, now Pat. No. 11,635,427, which is a continuation of application No. 15/415,276, filed on Jan. 25, 2017, now Pat. No. 10,761,090, which is a continuation of application No. 13/250,702, filed on Sep. 30, 2011, now Pat. No. 9,562,897.

(60) Provisional application No. 61/388,413, filed on Sep. 30, 2010.

(51) Int. Cl.
| | |
|---|---|
| *G01N 33/543* | (2006.01) |
| *B01F 33/3011* | (2022.01) |
| *B01F 33/302* | (2022.01) |
| *C12Q 1/6874* | (2018.01) |
| *C40B 30/04* | (2006.01) |
| *C40B 40/00* | (2006.01) |
| *C40B 40/04* | (2006.01) |
| *C40B 70/00* | (2006.01) |
| *G01N 33/532* | (2006.01) |

(52) U.S. Cl.
CPC ..... *G01N 33/54366* (2013.01); *C12Q 1/6874* (2013.01); *C40B 40/00* (2013.01); *C40B 40/04* (2013.01); *C40B 70/00* (2013.01); *G01N 33/532* (2013.01); *B01F 33/3011* (2022.01); *B01F 33/3021* (2022.01); *C40B 30/04* (2013.01)

(58) Field of Classification Search
None
See application file for complete search history.

(56) References Cited

U.S. PATENT DOCUMENTS

| | | | |
|---|---|---|---|
| 8,383,061 B2 | 2/2013 | Prakash et al. | |
| 9,714,937 B2 | 7/2017 | Dunaway | |
| 10,144,850 B2 | 12/2018 | Stender et al. | |
| 10,144,950 B2 | 12/2018 | Nolan | |
| 10,626,442 B2 | 4/2020 | Nolan | |
| 11,635,427 B2 * | 4/2023 | Samuels et al. | . G01N 33/54366 435/6.1 |
| 11,946,929 B2 * | 4/2024 | Samuels et al. | ........ C40B 70/00 |
| 2003/0148335 A1 | 8/2003 | Shen et al. | |
| 2004/0023271 A1 | 2/2004 | Kurn et al. | |
| 2006/0257893 A1 | 11/2006 | Takahashi et al. | |
| 2009/0092603 A1 | 4/2009 | Bamdad | |
| 2010/0041046 A1 | 2/2010 | Chiu et al. | |
| 2012/0220494 A1 | 8/2012 | Samuels et al. | |
| 2013/0143749 A1 | 6/2013 | Ghadessy et al. | |
| 2021/0230681 A1 | 7/2021 | Patterson et al. | |
| 2023/0417765 A1 | 12/2023 | Agresti et al. | |

FOREIGN PATENT DOCUMENTS

| | | |
|---|---|---|
| WO | 2011005221 A1 | 1/2011 |
| WO | 2012106385 A2 | 8/2012 |

OTHER PUBLICATIONS

Joerger et al., "Analyte Detection with DNA-Labeled Antibodies and Polymerase Chain Reaction," Clin. Chem. 1995, 41(9):1371-1377. (Year: 1995).*
Adler, 2008, Sensitivity by combination: immuno-PCR and related technologies, The Analyst 133(6):685-824.
Wang, 2010, Single Cell Analysis: the new frontier in 'omics', Trends in Biotech 28:281-90.
Lundberg, 2011, Homogenous antibody-based proximity extension assays provide sensitive and specific detection of low-abundant proteins in human blood, Nucleic Acids Res 39(15):e102.
Nam, 2003, Nanoparticle-based Bio-bar dodes for the ultrasensitive detection of proteins, Science 301:1884-1886.
Niemeyer, 2007, Detecting antigens by quantitative immuno-PCR, Nat Prot 2(8):1918-1930.

* cited by examiner

*Primary Examiner* — Kaijiang Zhang
(74) *Attorney, Agent, or Firm* — Thomas C. Meyers; Sullivan & Worcester LLP

(57) ABSTRACT

The invention generally relates to performing sandwich assays in droplets. In certain embodiments, the invention provides methods for detecting a target analyte that involve forming a compartmentalized portion of fluid including a portion of a sample suspected of containing a target analyte and a sample identifier, a first binding agent having a target identifier, and a second binding agent specific to the target analyte under conditions that produce a complex of the first and second binding agents with the target analyte, separating the complexes, and detecting the complexes, thereby detecting the target analyte.

17 Claims, 19 Drawing Sheets

Specification includes a Sequence Listing.

Modified Analytes (e.g. Post Translational-PTM)

DNA

Complex

RNA
Splice variant

Complex

RNA
Full length

Single Target

Protein:Nucleic Acid Complex

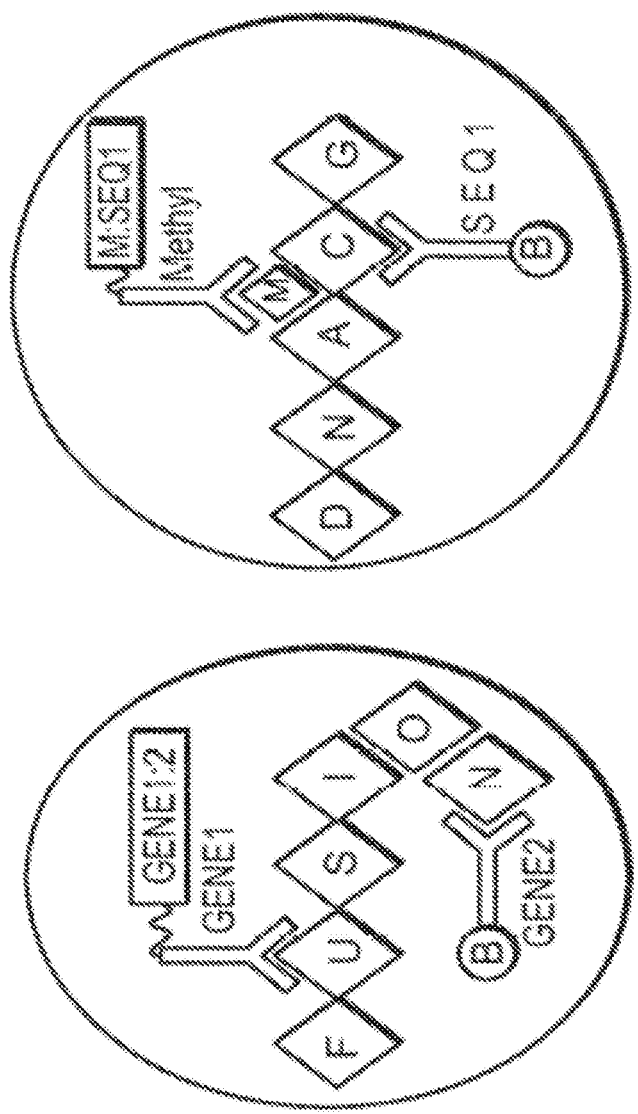

SANDWICH ASSAYS IN DROPLETS

SEQUENCE LISTING

A "Sequence Listing XML" is submitted herewith in XML file format and (i) the name of the file is RDT-549-US04-Seqs.xml; (ii) the date of creation is Apr. 24, 2023; and (iii) the size of the file is 13,439 bytes and the material in the XML file is incorporated by reference.

TECHNICAL FIELD

The invention generally relates to performing sandwich assays, advantageously in droplets.

BACKGROUND OF THE INVENTION

Biomarkers are commonly used to monitor and diagnosis disease. Biomarkers include nucleic acids, proteins, or other biological molecules. Typically, an assay to identify a disease-associated biomarker is conducted in biological media, such as human tissues, cells or fluids, and may be used to identify pathological processes before individuals become symptomatic or to identify individuals who are susceptible to diseases or already show signs and symptoms of a disease.

Standard screening assays have been developed that can detect bacteria or viruses. Similarly, standard screening assays have been developed that can use biomarkers to assess the health status of a patient and to provide insight into the patient's risk of having a particular disease or disorder. An exemplary class of screening assays are sandwich assay. In a sandwich assay, a first binding agent with specificity for a target analyte (e.g., a bacteria, virus, or biomarker) is bound to a solid support. A sample is introduced to the solid support such that target analyte in the sample binds the first binding agent, thus becoming immobilized to the solid support. Then, a second binding agent with specificity for a target analyte is introduced to the and allowed to bind to the immobilized target analyte. The assay is named a sandwich assay because the first and second binding agents now sandwich the target analyte. A wash step is performed to remove unbound components of the sample and any excess binding agents. The second binding agent typically includes a detectable label, and the label on the second binding agent is then detected, thus detecting the target analyte in the sample. Sandwich assays are typically antibody based and a commonly used sandwich assay is an enzyme-linked immunosorbent assay (ELISA).

A problem with sandwich assays, particularly antibody based sandwich assays, is that they are unable to scale to high-level multiplexing. Issues of antibody cross-reactivity and non-specific adsorption occur when assays are multiplexed in the same tube. The ability to multiplex samples, i.e., pool different patient samples, is important for decreasing costs and increasing the through-put of analysis platforms. Additionally, assay development requires significant effort to optimize reagents to retain similar sensitivity as in single-plex assays. Further, such assays are not practical for use with small sample amounts collected at clinics.

SUMMARY OF THE INVENTION

The invention utilizes microfluidics and droplet technology in combination with sandwich assays. Methods of the invention avoid the issues of antibody cross-reactivity and non-specific adsorption that occur when assays are multiplexed in bulk format. The use of droplets allows high levels of multiplexing while retaining the specificity of single-plex assays without the need for large sample volumes.

Methods of the invention involve forming a droplet that includes reagents for a sandwich assay (e.g., a first target binding agent having a differentially detectable identifier and a second target binding agent). Any technique known in the art for forming droplets may be used with methods of the invention. An exemplary method involves flowing a stream of reagent fluid such that it intersects two opposing streams of flowing carrier fluid. The carrier fluid is immiscible with the reagent fluid. Intersection of the reagent fluid with the two opposing streams of flowing carrier fluid results in partitioning of the reagent fluid into individual reagent droplets. The carrier fluid may be any fluid that is immiscible with the reagent fluid. An exemplary carrier fluid is oil. In certain embodiments, the carrier fluid includes a surfactant, such as a fluorosurfactant.

A sample containing target analyte (e.g., bacteria, virus, nucleic acid or protein) is introduced into a reagent droplet. This can occur by forming sample droplets and merging the sample droplets with the reagent droplets to form mixed droplets that include sample and reagents for the sandwich assay. Another technique involves contacting the reagent droplet with a fluid stream including the sample. Contact between the droplet and the fluid stream results in a portion of the fluid stream integrating with the droplet to form the mixed droplet.

Methods of the invention may be conducted in microfluidic channels. As such, in certain embodiments, methods of the invention may further involve flowing the droplet through a first channel and flowing the fluid stream through a second channel. The first and second channels are oriented such that the channels intersect each other. Any angle that results in an intersection of the channels may be used. In a particular embodiment, the first and second channels are oriented perpendicular to each other. Methods of the invention may further involve applying an electric field to the droplet and the fluid stream. The electric field assists in rupturing the interface separating the two sample fluids. In particular embodiments, the electric field is a high-frequency electric field.

After forming the mixed droplet, a sandwich assay is conducted in the droplet such that complexes of target analyte and first and second binding agents are formed. In certain embodiments, the assay is conducted in the presence of a competitive inhibitor. The competitive inhibitor has affinity to analytes in the sample that may compete for binding with the target analyte. The competitive inhibitor binds these competing analytes and ensures that they do not compete with the target analyte for binding to the binding agents.

Generally, the second binding agent is configured such that it can be coupled to a solid support. For example, a terminal portion of the second binding agent may be functionalized with a terminal amine such that it can covalently bind an epoxide coated surface. Alternatively, a terminal end of the second binding agent is functionalized with one member of a binding pair while a surface of the solid support is coated with the other member of the binding pair (e.g., biotin/avidin; biotin/streptavidin/or digoxigenin/anti-digoxigenin). The support may be a bead that is present in the droplet or it may be a substrate outside of the droplet. Generally, the complexes become immobilized on the solid support while uncomplexed sample components remain unbound in the sample.

Bead-bound complexes can be released from the droplets and separated from the unbound sample components. Alternatively, the droplet contents are released and the complexes become immobilized to a solid support. A wash step is performed to remove the unbound sample components, and then the target identifier associated with the first binding agent is detected.

The target identifier may be any type of differentially-detectable identifier, such as an optically detectable label (e.g., fluorescent or chemiluminescent label), radiolabel, electrochemical label, or a barcode label. Detection may be by any methods known in the art and the detection method will depend on the type of identifier used. The identifier may be releasably attached to the first binding agent or may be irreversibly attached to the first binding agent.

In particular embodiments, the identifier is a barcode sequence. The barcode sequences can be released from the first binding agents and then attached to each other to produce a single nucleic acid strand. This strand is then amplified (e.g., rolling circle amplification or PCR) and the amplified products are sequenced.

Sequencing may be by any method known in the art. In certain embodiments, sequencing is sequencing by synthesis. In other embodiments, sequencing is single molecule sequencing by synthesis. In certain embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes.

Another aspect of the invention provides reagent droplet libraries. Such libraries include a plurality of droplets containing the elements necessary for a sandwich assay prior to introduction of the target analyte. Preferably, droplets are surrounded by an immiscible carrier fluid, e.g., aqueous droplets surrounded by oil. Each droplet includes a first binding agent having a differentially detectable identifier and a second binding agent. The binding agents are any molecules that can bind a target analyte in a sample. Exemplary binding agents include DNA, RNA, LNA, PNA, proteins, antibodies, or aptamers. Each droplet may further include a sample identifier that can bind to the identifier linked to the first binding agent. In this manner, each droplet includes an identifier for a particular target analyte and an identifier for a specific droplet. Each droplet may further include a competitive inhibitor.

Other aspects and advantages of the invention are apparent upon consideration of the following detailed description thereof.

BRIEF DESCRIPTION OF DRAWINGS

FIG. 6A-FIG. 6J depict target analyte sandwiches with identifiers embodying principles of the invention.

DETAILED DESCRIPTION OF THE INVENTION

Figure 1:
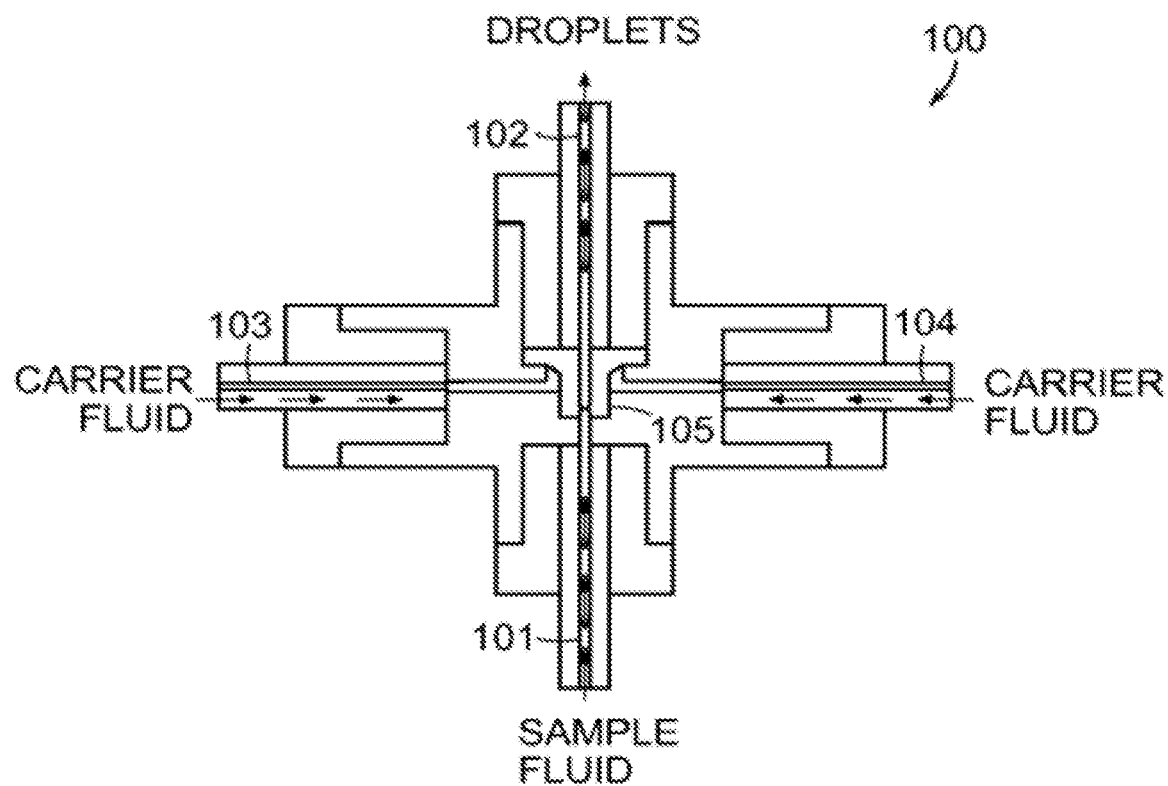
FIG. 1 is a drawing showing a device for droplet formation.

The invention generally relates to sandwich assays in droplets. In certain aspects, the invention provides methods for detecting and optionally quantifying a target analyte by forming a compartmentalized portion of fluid including a portion of a sample suspected of containing a target analyte, a first binding agent specific to the target analyte and having a target identifier, and a second binding agent specific to a different part of the target analyte under conditions that produce a complex of the first and second binding agents with the target analyte, separating the complexes from uncomplexed target identifiers, and detecting the complexes thereby detecting the target analyte. The invention allows for a high degree of multiplexing, thus allowing the use of multiple samples, targets or both. Moreover, the invention is useful to quantify targets as detailed below. There are numerous variations in terms of the manner in which devices and methods of the invention operate. A number of non-limiting examples are provided below. However, it is clear to one of skill in the art that numerous additional advantages and features of the invention are apparent upon consideration of the present specification and the examples that follow.

Samples

One of skill in the art will recognize that methods and systems of the invention are not limited to any particular type of sample, and methods and systems of the invention may be used with any type of organic, inorganic, or biological molecule. In particular embodiments the sample includes nucleic acid target molecules. Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid target molecules can be obtained from any cellular material, obtained from an animal, plant, bacterium, fungus, or any other cellular organism. In certain embodiments, the nucleic acid target molecules are obtained from a single cell. Biological samples for use in the present invention include viral particles or preparations. Nucleic acid target molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules can also be isolated from cultured cells, such as a primary cell culture or a cell line. The cells or tissues from which target nucleic acids are obtained can be infected with a virus or other intracellular pathogen. A sample can also be total RNA extracted from a biological specimen, a cDNA library, viral, or genomic DNA.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically is fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules can be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-C6H4-(OCH2-CH2)xOH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), beta-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments can be partitioned into fractions comprising a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, s-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

The invention is useful to detect and/or quantify other target molecules, such as any molecule that can be specifically bound in at least two distinct portions of the target or any molecule in complex with at least one other molecule that can be specifically bound by binding agents.

Droplet Formation

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

Figure 2:
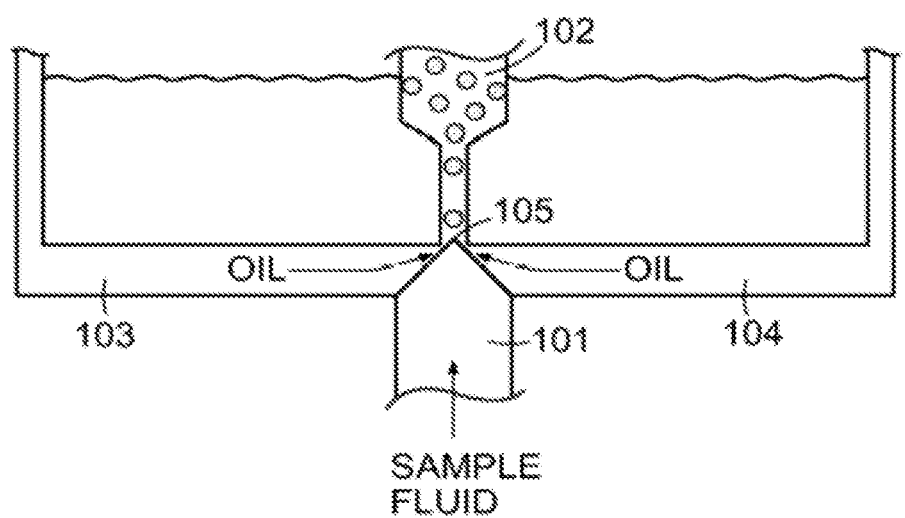
FIG. 2 is a drawing showing a device for droplet formation.
Figure 3B:
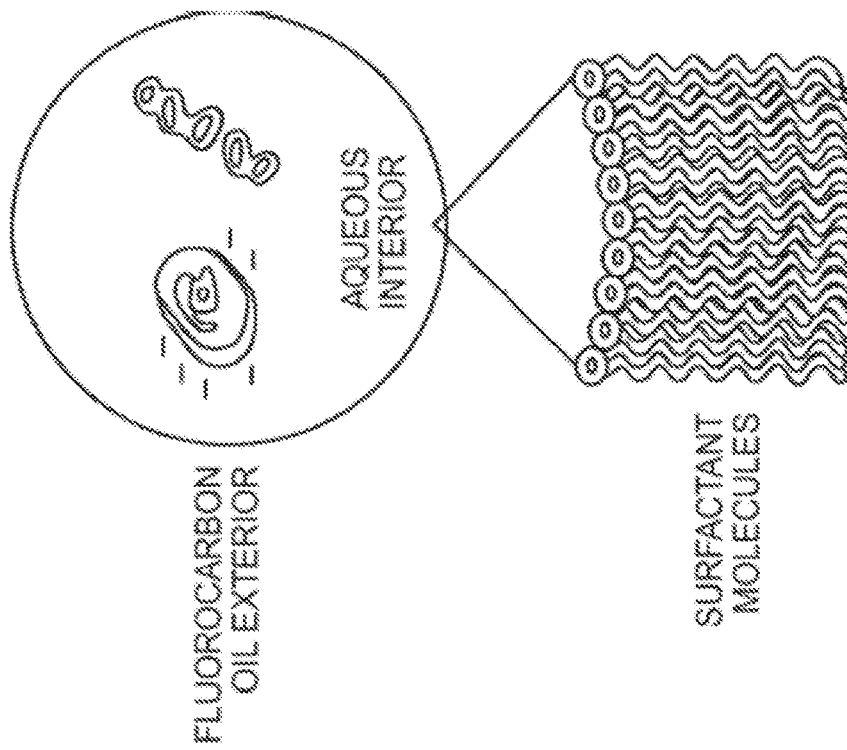
FIG. 3A-FIG. 3D depict droplet generation, merging, and combining of droplets in an embodiment of the invention.
Figure 3A:
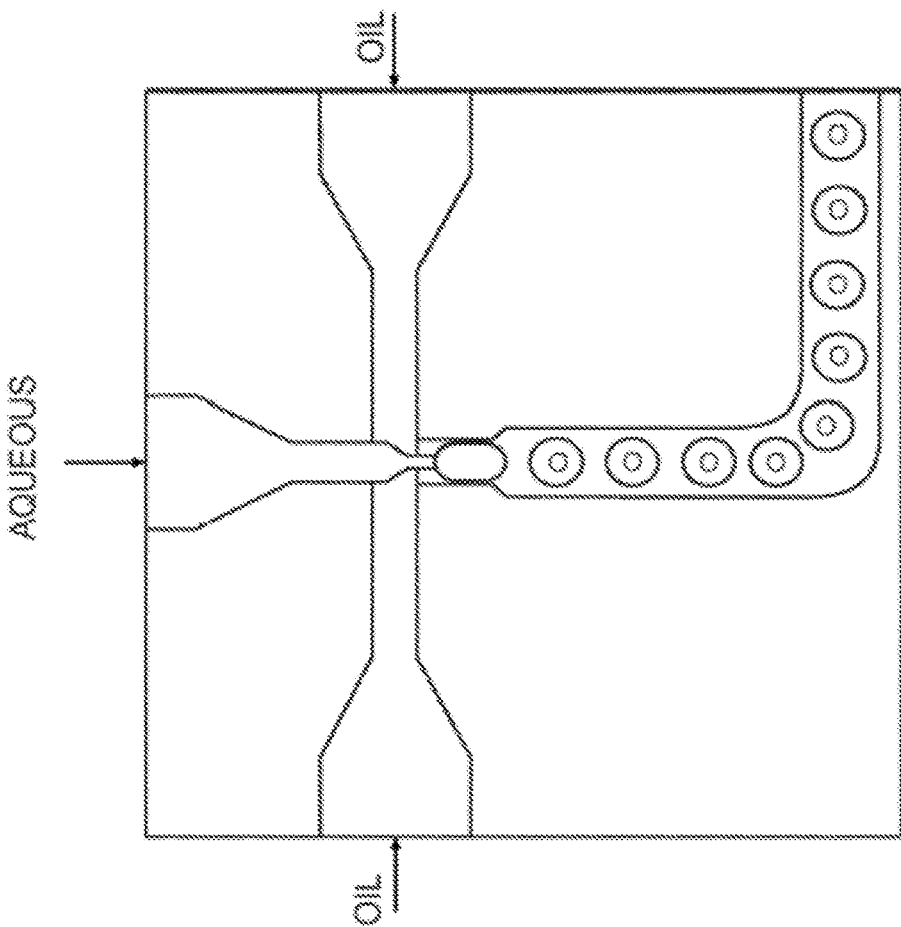
Figure 3C:
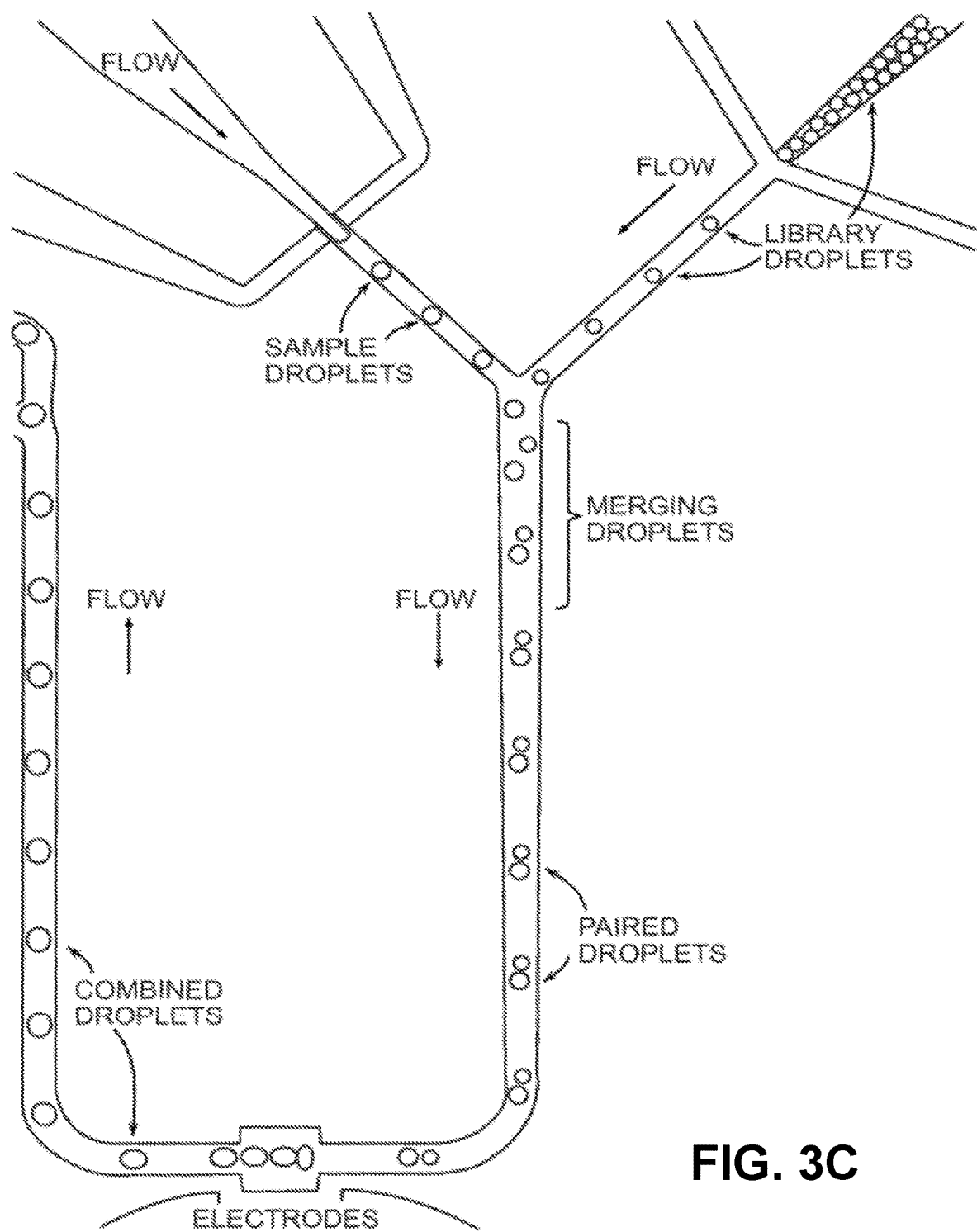
Figure 3D:
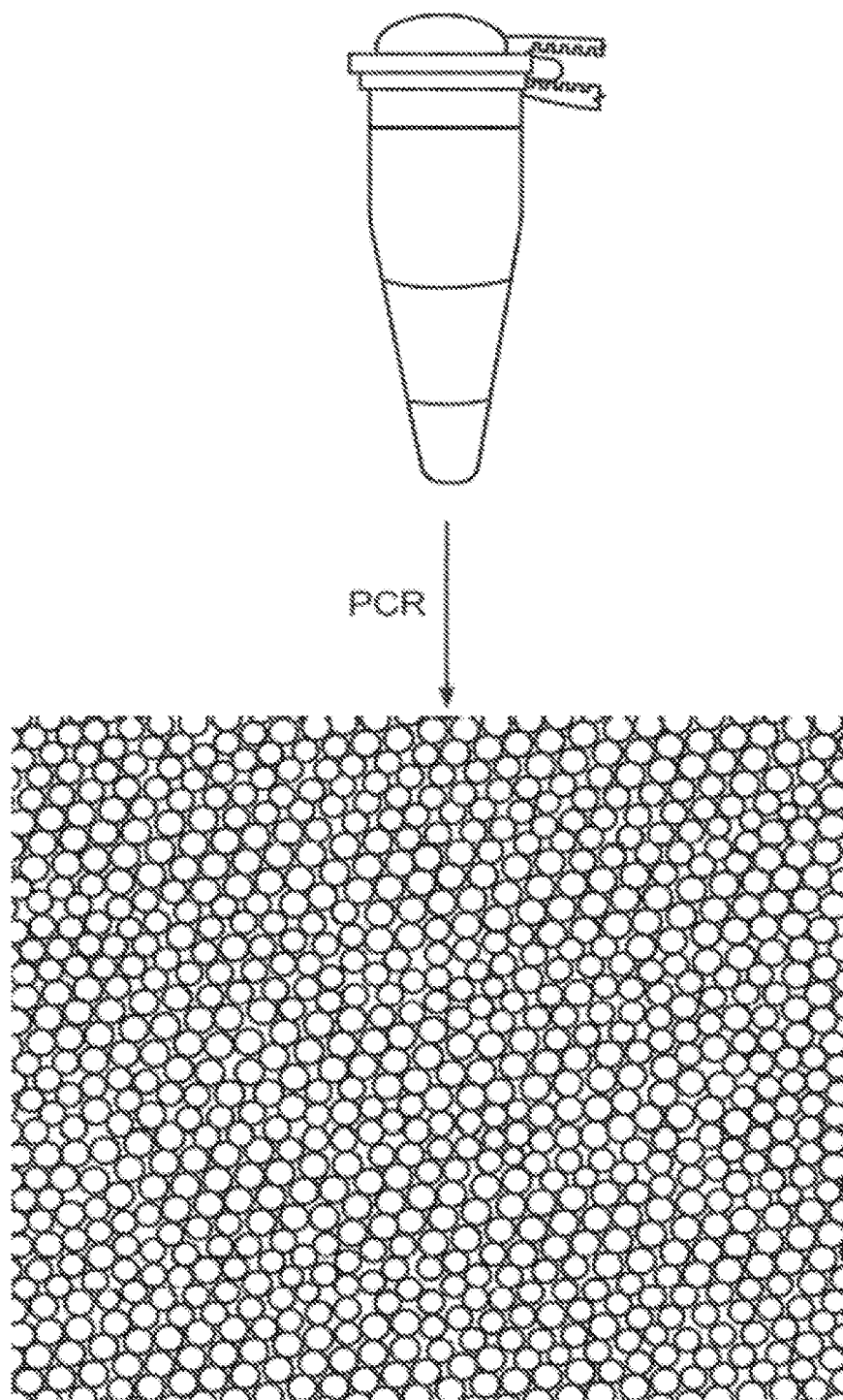
Figure 4A:
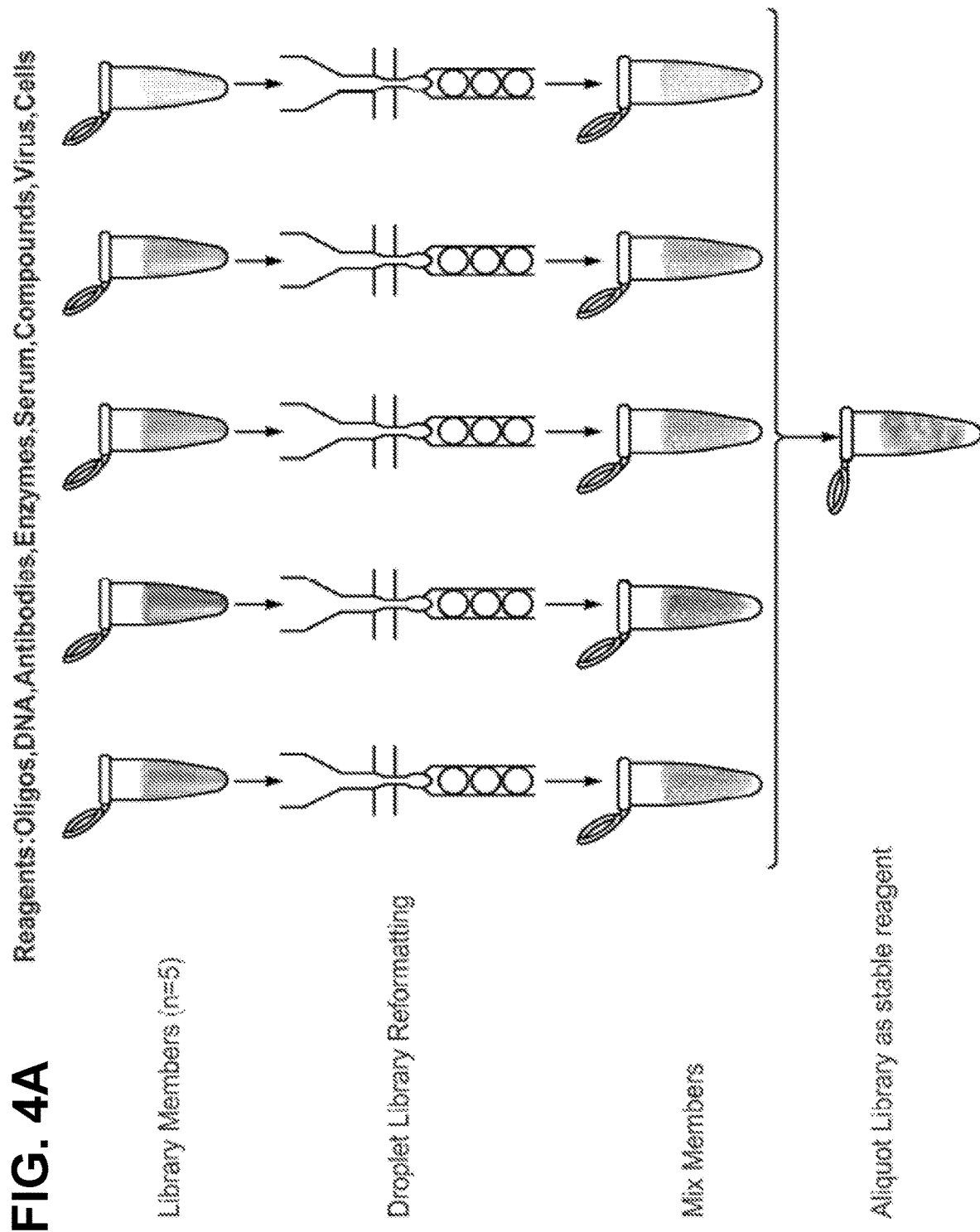
FIG. 4A-FIG. 4C depict droplet library formation in an embodiment of the invention.
Figure 4B:
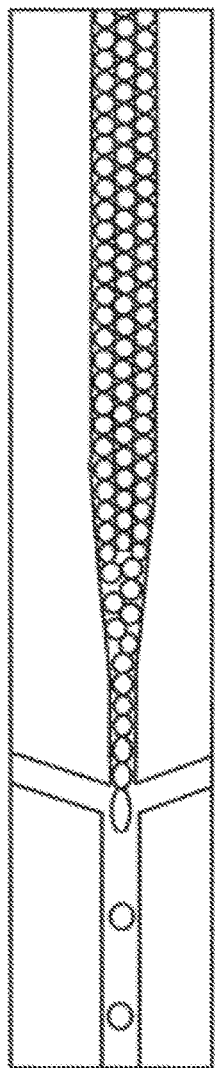
Figure 4C:
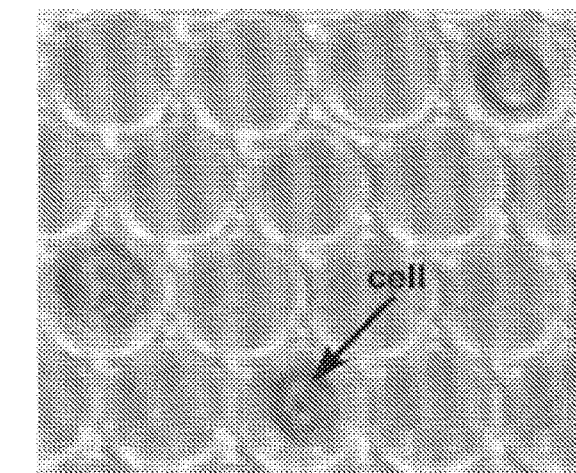
Figure 4C:
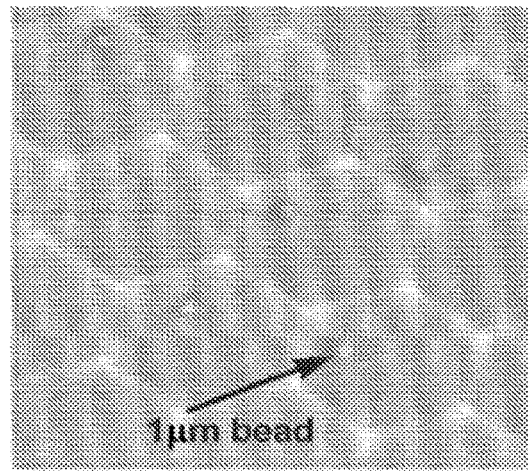

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

Another approach to merging sample fluids involves forming a droplet, and contacting the droplet with a fluid stream, in which a portion of the fluid stream integrates with the droplet to form a mixed droplet. In this approach, only one phase needs to reach a merge area in a form of a droplet.

A reagent droplet, or library of reagent droplets is formed as described above, and can be stored in a collection of other droplets for combining with samples after re-introduction into a microfluidic device. After formation of the reagent droplet, the droplet is contacted with a flow of a sample fluid stream. Contact between the reagent droplet and the fluid stream results in a portion of the sample fluid stream integrating with the reagent droplet to form a mixed droplet.

The monodisperse reagent droplets flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a sample fluid is protruding from an opening of the second channel into the first channel. Preferably, the channels are oriented perpendicular to each other. However, any angle that results in an intersection of the channels may be used.

The bolus of the sample fluid stream continues to increase in size due to pumping action of a positive displacement pump connected to channel, which outputs a steady stream of the second sample fluid into the merge area. The flowing reagent droplet eventually contacts the bolus of the sample fluid that is protruding into the first channel. Contact between the two fluids results in a portion of the sample fluid being segmented from the sample fluid stream and joining with the reagent fluid droplet to form a mixed droplet. In certain embodiments, each incoming droplet of reagent fluid is merged with the same amount of sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created using any suitable technique, for example, by placing the reagent droplet and the sample fluid within an electric field (which may be AC, DC, etc.), and/or causing a reaction to occur that causes the reagent droplet and the sample fluid to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the sample fluid and the droplet. Rupturing the interface facilitates merging of bolus of the s sample fluid and the reagent droplet. The forming mixed droplet continues to increase in size until it a portion of the sample fluid breaks free or segments from the sample fluid stream prior to arrival and merging of the next reagent droplet. The segmenting of the portion of the sample fluid from the sample fluid stream occurs as soon as the shear force exerted on the forming mixed droplet by the immiscible carrier fluid overcomes the surface tension whose action is to keep the segmenting portion of the sample fluid connected with the second sample fluid stream. The now fully formed mixed droplet continues to flow through the first channel.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with enzymes can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

The oil can comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) may be important to maintain the stability and integrity of the droplets and may also be beneficial for the subsequent use of the droplets within the library for the various biological and chemical assays described herein. Fluids (e.g., aqueous fluids, immiscible oils, etc.) and other surfactants that can be utilized in the droplet libraries of the present invention are described in greater detail herein.

Microfluidic Systems

Reagents can be reformatted as droplet libraries utilizing automated devices. Specifically, the library element components can be placed onto plates containing any number of wells, i.e. 96, 384, etc. The plates can then be placed in any one of a number of devices known in the art for forming the droplets. The droplets can be placed into a vial or other such container, containing the stable droplet library for later use. In general, the process aspirates the components from each well of a well plate and infuses them through tubing connected to a microfluidic device (described in greater detail herein) which can be used to form the droplets that constitute a single library member or 'element'. The tubing is rinsed at a wash station and then the process can be repeated to generate droplets for the next library element.

A collection vial can be used to contain the droplets made using the Automated Droplet Library Production. In one example, the collection vial has two holes, a first hole in the center of the vial cap and a second hole part way to the edge of the vial cap. The vial is first filled with oil through the second hole to purge air out first hole, the emulsion is then introduced to the vial through the first hole, typically this is done sequentially one library element at a time at low volume fraction, and oil is displaced and goes out through the second hole. The collected droplets can be stored in the vial for periods of time in excess of 3 months. To remove the emulsion for use or to make smaller aliquots, oil is introduced through the second opening to displace the emulsion and drive out the first opening.

The droplet libraries of the present invention are preferably formed by utilizing microfluidic devices and are preferably utilized to perform various biological and chemical assays on microfluidic devices, as described in detail herein. The present invention also provides embedded microfluidic nozzles. In order to create a monodisperse (<1.5% polydispersity) emulsion directly from a library well, a nozzle can be formed directly into the fitting used to connect the storage well/reservoir (e.g. syringe) to a syringe tip (e.g. capillary tubing). Examples of suitable nozzles to create the droplet libraries of the instant invention are described in WO 2007/081385 and WO 2008/063227.

Since the flow is three dimensional, under this design surface wetting effects are minimized. The nozzle can be made from one or two oil lines providing constant flow of oil into the nozzle, a connection to the capillary tubing, and a connection to the storage well/reservoir (e.g. syringe). The high resolution part of the nozzle can be made out of a small bore tubing or a small, simple part molded or stamped from an appropriate material (Teflon®, plastic, metal, etc). If necessary, the nozzle itself could be formed into the tip of the ferrule using post mold processing such as laser ablation or drilling.

This nozzle design eliminates the surface wetting issues surrounding the quasi-2D flow associated with typical microfluidic nozzles made using soft lithography or other standard microfluidic chip manufacturing techniques. This is because the nozzle design is fully 3-dimensional, resulting is a complete isolation of the nozzle section from the continuous aqueous phase. This same design can also be used for generation of emulsions required for immediate use, where the aqueous line would be attached directly to a syringe and the outlet of the nozzle would be used to transport the emulsion to the point of use (e.g. into a microfluidic PCR chip, delay line, etc).

In another embodiment, the present invention provides compositions and methods to directly emulsify library elements from standard library storage geometries (e.g. 96 well plates, etc). In order to create a monodisperse emulsion from fluids contained in a library well plate, this invention would include microfluidic based nozzles manufactured simultaneously with an appropriately designed fluidic interconnect or well.

Specifically, the microfluidic devices and methods described herein are based on the creation and electrical manipulation of aqueous phase droplets (e.g., droplet libraries) completely encapsulated by an inert immiscible oil stream. This combination enables precise droplet generation, highly efficient, electrically addressable, droplet coalescence, and controllable, electrically addressable single droplet sorting. The microfluidic devices include one or more channels and modules. The integration of these modules is an essential enabling technology for a droplet based, high-throughput microfluidic reactor system and provides an ideal system for utilizing the droplet libraries provided herein for numerous biological, chemical, or diagnostic applications.

Substrates

The microfluidic device of the present invention includes one or more analysis units. An "analysis unit" is a microsubstrate, e.g., a microchip. The terms microsubstrate, substrate, microchip, and chip are used interchangeably he, ein. The analysis unit includes at least one inlet channel, at least one main channel and at least one inlet module. The analysis unit can further include at least one coalescence module. at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227.

A variety of materials and methods can be used to form any of the described components of the systems and devices of the invention. For example, various components of the invention can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or Teflon®, or the like, or thermoplastic polyers.

Silicone polymers are preferred, for example, the silicone elastomer polydimethyl siloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in Duffy et al., "Rapid Prototyping of Microfluidic Systems and Polydimethylsiloxane," Anal. Chem., 70:474-480, 1998.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

Channels

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel).

In embodiments where the channel is completely covered, at least one portion of the channel can have a cross-section that is completely enclosed, and/or the entire channel may be completely enclosed along its entire length with the exception of its inlet and outlet.

The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

A "main channel" is a channel of the device of the invention that permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets. The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells). To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

Fluids

The fluids described herein are related to the fluids within the droplet libraries and to the fluids within a microfluidic device. The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

According to the invention, a fluidic stream may be continuous and/or discontinuous. A "continuous" fluidic stream is a fluidic stream that is produced as a single entity, e.g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar (potentially including streams of two or more fluids), or turbulent in some cases.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. In some embodiments, the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof Various labels and means for detection are described in greater detail herein.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The 15 average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 µm (e.g., 0.1, 0.2 . . . 5, 10, 15, 20, 25, 30, 35, 40, 45, 50 . . . 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; WO 2006/040554; WO 2004/002627; WO 2004/091763; WO 2005/021151; WO 2006/096571; WO 2007/089541; WO 2007/081385 and WO 2008/063227.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle. Droplets of a sample fluid can be formed within the inlet module on the microfluidic device or droplets (or droplet libraries) can be formed before the sample fluid is introduced to the microfluidic device (stable droplet libraries can be stored after manufacturing, for introduction onto the microfluidic device and combination with sample droplets or other droplet libraries). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

Surfactants

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A very large body of fundamental research and commercial application development exists for non-fluorous surfactants and emulsions ranging from sub-micron droplets to very large, macroscopic emulsions. In contrast, fundamental knowledge and commercial practice with fluorinated oils and surfactants is much less common. More specifically, testing and development of fluorosurfactants and fluorous oil formulations for the application of creating large libraries of micron-scale droplets with unique composition is limited to only a few groups throughout the world. Only a few commercially available fluorosurfactants that stabilize water-in-fluorocarbon oil emulsions exist. For instance, surfactants with short fluorotelomer-tails (typically perfluorinated C6 tO C10) are available, but they do not provide sufficient long-term emulsion stability. Fluorosurfactants with longer fluorocarbon tails, such as perfluoropolyether (PFPE), are limited to molecules with ionic headgroups.

Classes of oils are available from wide variety of fluorinated oils and are available from commercial sources. The requirements for the oil are (1) immiscibility with the aqueous phase, (2) solubility of emulsion stabilizing surfactants in the oil, and (3) compatibility and/or insolubility of reagents from the droplet phase. Oils include hydrofluoroethers, which are fluorinated alkyl chains coupled with hydrocarbon chemistry through and ether bond. One supplier of this type of oil is 3M.

The products are marketed as Novec Engineered Fluids or HFE-series oils. This oils include but are not limited to, HFE-7500, which is a preferred embodiment as it provides superior droplet stability seems to be higher. Other oils include FIFE-7100, -7200, -7600, which are examples of other HFEs available from 3M. These can be used as stand-alone oils or components of oil mixtures to optimize emulsion properties and performance. Other hydrofluoroethers are also available from other producers, distributors, or resellers may offer hydrofluoroethers. Another class of oil is perfluoroalkylamines, which are perfluorinated oils based on perfluoroalkyl amine structures. 3M produces these oils as Fluorinert Electronic Liquids (FC-oils). Fluorinert products differ by variations in alkyl chain length, branch structure, and combinations of different structures or pure oils. Many of them offer the potential for stand-alone oils or components of oil mixtures to optimize emulsion properties and performance. Specific examples are Fluorinert FC-3283, Fluorinert FC-40, which are a preferred embodiments.

Higher viscosity and boiling point useful for applications requiring elevated temperature (e.g., thermocyling for PCR). Other Fluorinert series can be used for stand-alone oils or components of oil mixtures to optimize emulsion properties and performance. Again, other perfluoroalkylamines are available from other producers, distributors, or resellers may offer perfluoroalkylamines.

Fluorinated organics/solvents offer a number of perfluorinated or partially fluorinated solvents are available from a variety of producers, distributors, and/or resellers. Many of them offer the potential for stand-alone oils or components of oil mixtures to optimize emulsion properties and performance. Examples of fluorinated organic reagents utilized, included (but not limited to) trifluoroacetic acid and hexafluoroisopropanol, to improve droplet stability in other fluorinated oil systems. Addtionally, fluoropolymers may also be used within a microfluidic system. Examples of fluoropolymers include, Krytox GPL oils, Solvay Galden oils, and other liquid fluoropolymers. Other fluorinated materials find widespread use in a variety of industries, but they are generally not well-known in the disciplines of interfacial, colloidal, physical, or synthetic organic chemistry. Therefore, a number of other candidates for oils exist in specialty and niche market applications. As such, new oils have been targeted partially that are perfluorinated materials, which are not widely recognized.

The properties of oils selected are based upon their chemical properties, such as, among others molecular structure, fluorine content and solvating strength. Physical properties of oils examined include viscosity, boiling point, thermal expansion coefficient, oil-in-water solubility, water-in-oil solubility, dielectric constant, polarity, and oil-in-water surface tension.

Classes of surfactants include fluorosurfactants that can be categorized by the type of fluorophilic portion of the molecule, the type of hydrophilic, or polar, portion, and the chemistry used to link the different parts of the molecule. Materials developed are capable of stabilizing an emulsion or droplet library. The preferred embodiment is the EA surfactant. Specifically, the EA surfactant is a Krytox-PEG-Krytox. The EA surfactant is a nonionic tri-block copolymer surfactant was developed to avoid issues that the ionic surfactants (e.g., RR, see below) which result from the use of some other ionic surfactant. Specifically, ionic surfactants interact with charged species in the droplets and can sequester ions (e.g., magnesium required for the PCR reaction) or other reagents to the oil phase. The structure of the EA surfactant comprises a PEG—approximately 600 Da with amine end functionality, PFPE—Mn is—5000-8000 from a Krytox FSH starting material and the linker is an amide coupling. Another surfactant includes the RR surfactant, which is a Krytox ammonium carboxylate. Alternative materials are alternative fluorophilic portion, i.e., PFPE (Solvay or Demnum), Poly(fluoroalkylacrylate) and other non-polymeric and partially fluorinated materials. Alternative headgroup chemistry for the hydrophilic portion includes, nonionic head groups like PEG (Mw, Mw/Mn (PDI)) and functionality (i.e., diblock, triblock and dendritic). Others include morpholino. Ionic head groups for the hydrophilic portion include anionic, such as elemental and amine salts and further cationic head portions. Other head group chemistries include zwitterionic, hybrid (e.g., PEG ionic and zonyl FSO/FSN), lipophilic (e.g, lipophilic to promote bilayer and lipophilic spacer to hydrophile). Another alternative is alternative coupling chemistry such as, phosphoryl/Friedel-Crafts, spacer to organic handle and others.

Characteristics of surfactants are their molecular structure, determined by NMR, chromatography (e.g., HPLC, GPC/SEC), FTIR, mass spectrometry, and titrations. Purity of surfactants is another characteristic examined in addition to the fluorophile-hydrophile balance.

A preferred embodiment includes oil-surfactant formulation for the application of library emulsions is R-oil (HFE-7500) mixed with 2 wt % EA surfactant ("REAM"). Concentrations of EA or RR surfactant at 0.1 wt % or lower to 5% or greater. Other formulations of oils and surfactants and other components added to the aqueous phase are used to improved and optimized the performance of the droplets performance. Those properties of the oil-surfactant mixture include simple mixtures (i.e., one oil and one surfactant, with varied surface concentration), co-surfactants, oil mixtures and additives, such as zonyl and TFA. Oil and surfactant mixture properties include surfactant solubility, critical micelle concentration (CMC), surfactant diffusivity, and interfacial tension, i.e., dynamic and equilibrium. Emulsion properties are also accounted for, those properties include size (absolute and size distribution), stability, transport, and biocompatibility. Stability relates directly to the coalesced droplets and their deformability/breaking and shredding ability. More particularly, the stability of the droplets in their generation, storage and shipping.

In general, production of surfactant and oils begins with the synthesis of surfactants and starting materials, such as PEG-diamine, EA and RR and also accounts for the purification processes, characterization, quality control, mixing and packaging. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

In another embodiment, a quaternary ammonium salt at the terminus of a hydrophilic oligomer is linked to a perfluoropolyether tail as shown in the following formula:

PFPE-C(O)NH—CH2CH2CH2-(OCH2CH2)30-CH2CH2CH2-N(CH3)3+I—. Some specific molecular features of the present invention include, but are not limited to, PFPE is from Krytox 157 FSH (Mn-6500), amide bond linking PFPE to hydrophile, propyl group immediately adjacent to the amide, propyl group immediately adjacent to the trimethylamino terminus. Specific structural formations can alter performance relationships, for example, PFPE chain is sufficiently long for molecule to be soluble in perfluorinated oils, amide linker provides hydrolytic stability and hydrogen bonding site, and a combination of PEG and quaternary ammonium cation provide high anchoring strength to the aqueous phase as well as electrostatic repulsion and steric hindrance to minimize reagent transport.

Variables in the molecular structure include, but are not limited to, PFPE molecular weight and polydispersity, PFPE structure, alternative perfluorinated tail chemistries, PEG molecular weight and polydispersity, shorter hydrocarbon linkers (ethyl or methyl versus propyl), longer hydrocarbon spacers (C4 or higher), alternative counterions, such as monovalent anions, monovalent, polyatomic anions and di- or tri-valent counterions (to produce two or more tail fluorosurfactants). Further variables in the molecule structure include alternative linker chemistries (e.g., ether, ester, etc), alternative hydrophilic oligomers (e.g., polyalcohol, polyacrylamide, etc.), alternative quaternary ammonium cations, and alternative ionic groups (e.g., anionic terminus—carboxylate etc.; alternative cations).

The present invention is also directed to the coupling of PEG-diamines with carboxylic acid-terminated perflouropolyether (Krytox 157) to form surfactants. Specifically, the present invention is directed to a fluorosurfactant molecule made by the ionic coupling of amine-terminated polyethyleneglycol (PEG-amine) with the carboxylic acid of DuPont Krytox perfluoropolyether (PFPE). The resulting structure conveys good performance in the stabilization of aqueous droplets in fluorinated oil in a microfluidic system. Preferred surfactants are described in WO 2008/021123. The present invention provides droplets with a fluorosurfactant interface separating the aqueous droplet and its contents from the surrounding immiscible fluorocarbon oil. In one example, DNA amplification reactions occurring inside these droplets generate material that does not interact with the channel walls, and collection of the DNA-containing droplets for subsequent manipulation and sequencing is straightforward. This technology provides a solution for amplification of DNA from single cells, allowing for both genotyping and whole genome amplification. In addition, use within a microfluidic device or platform as described herein achieves very high throughput, with droplets processed at rates in excess of 5000 droplets per second, enabling greater than $1\times10^6$ single-cell droplets to be formed and manipulated per hour.

Other examples of materials related to this invention include the formation of salts made by combination of various primary, secondary, or tertiary amines with PFPE carboxylic acid. The resulting amphiphilic structure could be useful as a stand-alone surfactant or a co-surfactant. Similarly, fluorinated materials with carboxylic acids other than Krytox PFPE could be used to form ionic fluorosurfactants with various amine containing compounds.

Alternative amine-containing compounds for use with the present invention include, but are not limited to, PEG-monoamine (molecular weights range from 200 to 1,000,000 or more), PEG-diamine (molecular weights range from 200 to 1,000,000 or more), Multifunctional PEG amines (e.g., branched or dendritic structures), other hydrophilic polymers terminated with amines. Sugars include, but are not limited to, Sugars, Peptides, Biomolecules, Ethanolamine or Alkyl amines—primary, secondary, or tertiary (e.g., triethylamine, trimethylamine, methylamine, ethylamine, butylamine).

Alternative fluorinated groups for use with the present invention include, but are not limited to, Krytox FSL and FSM (alternative molecular weights), Demnum PFPE materials, Fluolink PFPE materials or Fluorinated small molecules with carboxylic acids.

The data described herein show that the fluorosurfactants comprised of PEG amine salts provide better performance (compared to other fluorosurfactants) for stabilization of aqueous droplets in fluorinated oils in droplet-based microfluidics applications. These novel surfactants are useful either in combination with other surfactants or as a stand-alone surfactant system.

Driving Forces

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Pat. No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure or other positive pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; WO 2006/040554; WO 2004/002627; WO 2004/091763; WO 2005/021151; WO 2006/096571; WO 2007/089541; WO 2007/081385 and WO 2008/063227; U.S. Pat. No. 6,540,895 and U.S. Patent Application Publication Nos. 20010029983 and 20050226742.

Droplet Inlet

The microfluidic device of the present invention includes one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules introducing droplets of samples into the main channel. For example, a first inlet module may introduce droplets of a first sample into a flow of fluid in the main channel and a second inlet module may introduce droplets of a second sample into the flow of fluid in main channel, and so forth. The second inlet module is preferably downstream from the first inlet module (e.g., about 30 Inn). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

Droplet Interdigitation

Particular design embodiments of the microfluidic device described herein allow for a more reproducible and controllable interdigitation of droplets of specific liquids followed by pair-wise coalescence of these droplets, described in further detail herein. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. The term "interdigitation" as used herein means pairing of droplets from separate aqueous streams, or from two separate inlet nozzles, for eventual coalescence.

Various nozzle designs enhance the interdigitation of droplets and further improves coalescence of droplets due to the better control of the interdigitation and smaller distance between pairs of droplets. The greater control over interdigitation allows for a perfect control over the frequency of either of the droplets. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle). Examples of preferred nozzle designs are as described in WO 2007/081385 and WO 2008/063227.

Droplet Coalescence or Combination

The microfluidic device of the present invention also includes one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity fuse, coalesce or combine their contents. The coalescence module can also include an apparatus, for generating an electric force.

The electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

The electric field can be generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

Preferred electrodes and patterned electrically conductive layers are described in WO 2007/081385 and WO 2008/063227 and can be associated with any module of the device (inlet module, coalescence module, mixing module, delay module, detection module and sorting module) to generate dielectric or electric forces to manipulate and control the droplets and their contents.

Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces.

Likewise, the polarizability of droplets also depends upon their size, shape and composition. For example, droplets that contain salts can be polarized. According to formulas provided in Fiedler, et al. Analytical Chemistry 70, 1909-1915 (1998), individual manipulation of single droplets requires field differences (inhomogeneities) with dimensions close to the droplets.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. Analytical Chemistry, 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

The electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

As described, an electric field may be applied to fluidic droplets to cause the droplets to experience an electric force. The electric force exerted on the fluidic droplets may be, in some cases, at least about $10^{-16}$ N/micrometer3. In certain cases, the electric force exerted on the fluidic droplets may be greater, e.g., at least about $10^{-15}$ N/micrometer3, at least about $10^{-14}$ N/micrometer3, at least about $10^{-13}$ N/micrometer3, at least about $10^{-12}$ N/micrometer3, at least about $10^{-11}$ N/micrometer3, at least about $10^{-10}$N/micrometer3, at least about $10^{-9}$ N/micrometer3, at least about $10^{-4}$ N/micrometer3, or at least about $10^{-7}$ N/micrometer3 or more. The electric force exerted on the fluidic droplets, relative to the surface area of the fluid, may be at least about $10^{-15}$N/micrometer2, and in some cases, at least about $10^{-14}$ N/micrometer2, at least about $10^{-13}$ N/micrometer2, at least about $10^{-12}$N/micrometer2, at least about $10^{-u}$N/micrometer2, at least about $10^{-m}$N/micrometer2, at least about $10^{-9}$ N/micrometer2, at least about $10^{-8}$ N/micrometer2, at least about $1e$ N/micrometer2, or at least about $10^{-6}$ N/micrometer2 or more. In yet other embodiments, the electric force exerted on the fluidic droplets may be at least about $10^{-9}$N, at least about $10^{4}$ N, at least about $10^{-7}$N, at least about $10^{-6}$N, at least about $10^{-5}$N, or at least about $10^{-4}$ N or more in some cases.

Binding Agents, Solid Supports, and Washing

Methods of the invention involve use of first and second binding agents (also called 'binders') that can bind to the target analyte to form a sandwich complex. The first and second binding agents have specificity for different binding sites on the same target analyte, i.e., the first and second binding agents bind different parts of the target analyte, where the analyte can be a single molecule or a stable complex of molecules. The binding agents may be any molecules that specifically bind to a target analyte in the sample. Exemplary binding agents include an antibody, an oligonucleotide, any protein based or nucleic acid based binding agent, or any agent capable of attaching to target analytes. Further binding agents embodied in methods of the invention include DNA, RNA, LNA (locked nucleic acids), PNA (peptide nucleic acid), a ligand, an irreversible inhibiting small molecule, a metabolite, a lipid, a sugar, a synthetic polymer, or other non-peptide or nucleic acid-based binding agent, or combinations of the above.

In certain embodiments, the binding agent is an antibody. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4): 145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

In certain embodiments, the binding agent is an aptamer. As used herein, "aptamer" and "nucleic acid ligand" are used interchangeably to refer to a nucleic acid that has a specific binding affinity for a target molecule, such as a protein. Like all nucleic acids, a particular nucleic acid ligand may be described by a linear sequence of nucleotides (A, U, T, C and G), typically 15-40 nucleotides long. Nucleic acid ligands can be engineered to encode for the complementary sequence of a target protein known to associate with the presence or absence of a specific disease.

In solution, the chain of nucleotides form intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Aptamers used in the compositions of the invention depend upon the target tissue. Nucleic acid ligands may be discovered by any method known in the art. In one embodiment, nucleic acid ligands are discovered using an in vitro selection process referred to as SELEX (Systematic Evolution of Ligands by Exponential enrichment). See for example Gold et al. (U.S. Pat. Nos. 5,270,163 and 5,475,096), the contents of each of which are herein incorporated by reference in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. There have been numerous improvements to the basic SELEX method, any of which may be used to discover nucleic acid ligands for use in methods of the invention.

In certain embodiments, the binding agent is an oligonucleotide. Methods of synthesizing oligonucleotides are known in the art. See, e.g., Sambrook et al. (DNA microarray: A Molecular Cloning Manual, Cold Spring Harbor, N.Y., 2003) or Maniatis, et al. (Molecular Cloning: A Laboratory Manual, Cold Spring Harbor, N.Y., 1982), the contents of each of which are incorporated by reference herein in their entirety. Suitable methods for synthesizing oligonucleotide probes are also described in Caruthers (Science 230:281-285, 1985), the contents of which are incorporated by reference. Oligonucleotides can also be obtained from commercial sources such as Operon Technologies, Amersham Pharmacia Biotech, Sigma, and Life Technologies. The oligonucleotides can have an identical melting temperature. The lengths of the probes can be extended or shortened at the 5' end or the 3' end to produce oligonucleotides with desired melting temperatures. Also, the annealing position of each oligonucleotide can be designed such that the sequence and length of the probe yield the desired melting temperature. The simplest equation for determining the melting temperature of probes smaller than 25 base pairs is the Wallace Rule ($Td=2(A+T)+4(G+C)$). Computer programs can also be used to design oligonucleotides, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting temperature) of each probe is calculated using software programs such as Oligo Design, available from Invitrogen Corp.

In certain embodiments, the oligonucleotides can include two portions, a portion that includes a nucleotide sequence with substantial complementarity to a target analyte, so that the oligonucleotide hybridizes with the target analyte. The oligonucleotidescan also include a universal region, i.e., a synthetic sequence that is not found in the genome of the organism of interest and that is identical in all of the oligonucleotides. The universal sequence may be a homopolymer, e.g., poly(A) or may be a sequence composed of many different bases. The universal region of the oligonucleotides is useful as a primer site for conducting secondary enzymatic reactions to link any number of sequence based or chemical moieties that are relevant to downstream processing and analysis.

Oligonucleotides suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA. Also included are nucleotides modified for use in photo-activated ligation or cleavage, e.g. 4-thiothymidine, 1-[2-Nitro-5-(6-trifluoroacetylcaproamidomethyl)phenyl]-ethyl-[2-cyanoethyl-(N,N-diisopropyl)]-phosphoramidite, 5-carboxyvinyl-2'-deoxyuridine.

The length of the nucleic acid binding agents are not critical, as long as they are capable of specific binding to the target regions. In fact, oligonucleotides may be of any length. For example, oligonucleotides may be as few as 5 nucleotides, or as much as 5000 nucleotides. Exemplary oligonucleotides are 5-mers, 10-mers, 15-mers, 20-mers, 25-mers, 50-mers, 100-mers, 200-mers, 500-mers, 1000-mers, 3000-mers, or 5000-mers. Methods for determining an optimal oligonucleotides length are known in the art. See, e.g., Shuber (U.S. Pat. No. 5,888,778). The first and second binding agents do not have to be of the same length. In certain embodiments, the first and second binding agents are the same length, while in other embodiments, the first and second binding agents are of different lengths.

Figure 7:
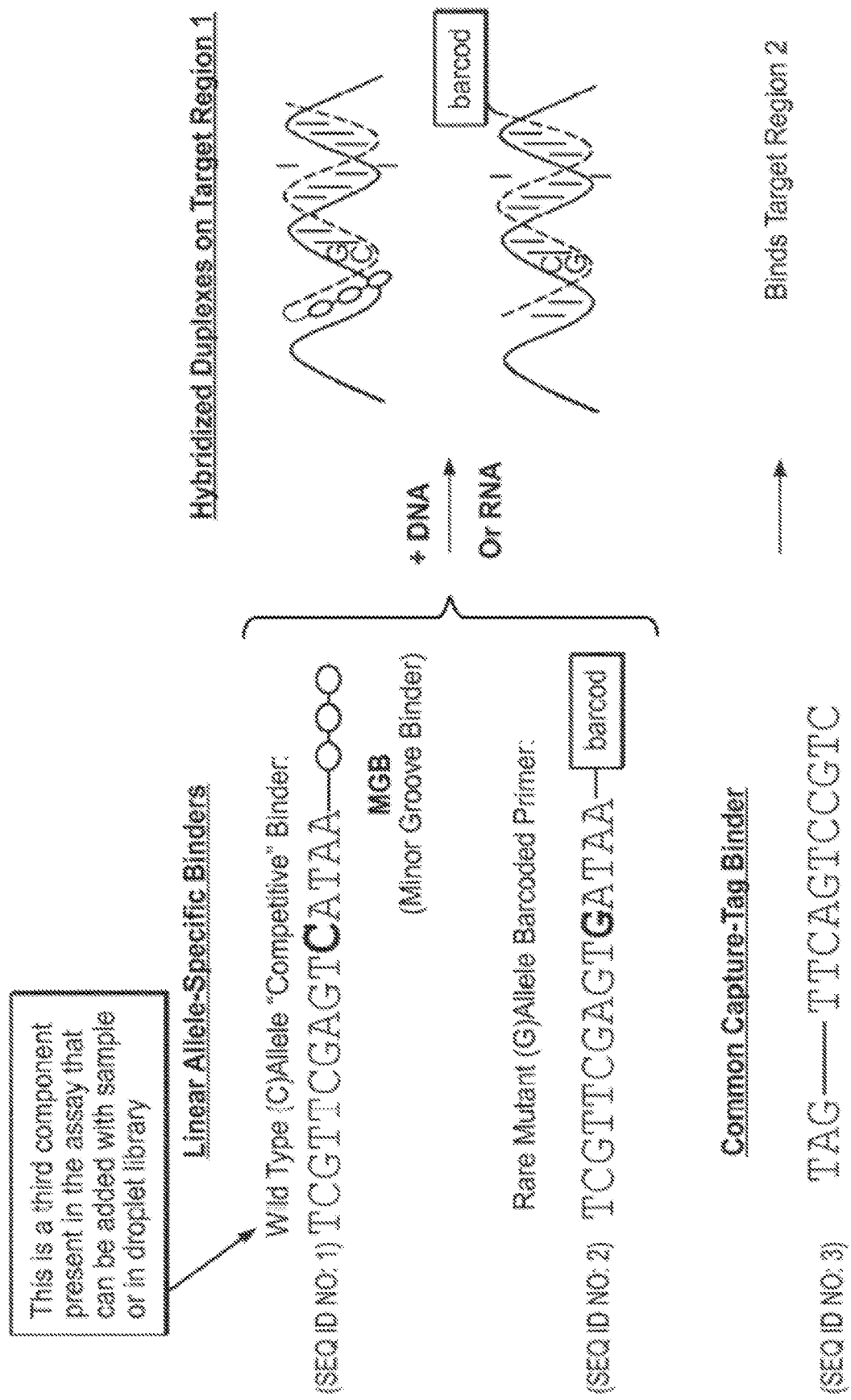
FIG. 7 depicts a competitive inhibitor from one embodiment of the invention.

In certain embodiments, a competitive inhibitor is introduced to the droplet library or the sample in order to enhance the specificity of the isolated sandwich formation. In some embodiments, the sample contains target analytes and unspecific analytes similar to the target analytes which may result in a false positive connection between the binding agent specific to the target analyte and the unspecific analyte. If a false positive connection is made, the representative value of the identifiers to the target analyte reduces in specificity. In one embodiment unspecific nuclei acid analytes may contain a sequence with a single base difference in a sequence. Unspecific analytes include any difference from a target protein or nucleic acid or other target analyte that would result in an affinity of the target analyte identifier to the unspecific analyte. FIG. 7 depicts a non-limiting embodiment of the use of a competitive inhibitor to prevent a binding agent with an identifier and, or a capture molecule from binding to a competitive unspecific analyte, wild type (C) allele, within the sample, when the target analyte is a rare mutant (G) allele. In the FIG. 7 embodiment, the competitive inhibitor includes a minor groove binder motif that increases the affinity to the wild type unspecific analyte, and binds to the unspecific analyte prior to the target analyte specific binding agent, or competes the target analyte specific binding agent off. Methods of the invention provide for the competitive inhibitor to be DNA, RNA, PNA, and LNA, and any other nucleic acid, or protein, or other binding agents capable of preventing false positive attachment to a unspecific analyte. The competitive molecules can be included in the sample, the droplet library, or both.

Generally, the second binding agent (also called the 'capture-tagged binder') is configured such that it can be coupled to a solid support in either a reversible or irreversible manner. For example, a terminal portion of the second binding agent may be functionalized with a terminal amine such that it can covalently bind an epoxide coated surface. The terminal amine that can form a covalent bond with an epoxide coated bead. In this embodiment, the epoxide coated bead is introduced to the binding agent now bearing an amine group. The highly-reactive epoxide ring opens, and a reactive carbon binds to the amine group on the copy. Further description of amine attachment is shown for example in Harris et al. (U.S. Pat. No. 7,635,562; Joos et al., Analytical Biochemistry 247:96-101, 1997; Oroskar et al., Clin. Chem. 42:1547-1555, 1996; and Khandjian, Mol. Bio. Rep. 11:107-115, 1986, the content of each of which is incorporated by reference herein in its entirety.

Alternatively, a part of the second binding agent is functionalized with one member of a binding pair while a surface of the solid support is functionalized with the other member of the binding pair (e.g., biotin/avidin; biotin/streptavidin/or digoxigenin/anti-digoxigenin). The second binding agent, now functionalized with a member of the binding pair (i.e., member of a capture tag pair) is brought into proximity of the solid support coated with the other member of the binding pairs. The two members of the binding pair interact to immobilize the complexes onto the solid support. See Harris et al. U.S. Pat. No. 7,635,562; Taylor et al., J. Phys. D. Appl. Phys. 24:1443, 1991); and Smith et al., Science 253:1122, 1992, the content of each of which is incorporated by reference herein in its entirety. Additional stringency can be provided through using tandem binding motif pairs.

Exemplary couplings include but are not limited to 1) a biotin capture tag for use with a streptavidin, avidin, or alternative modified derivatives of streptavidin or avidin solid supports; 2) a desthiobiotin capture tag for use with a streptavidin, avidin, or alternative modified derivatives of streptavidin or avidin solid support; 3) an antigen capture tag including FLAG, hemagglutinin, calmodulin-binding domain, histidinemultimers, or other common epitope tags for use with their cognate binding partners including anti-FLAG, anti-hemagglutinin, anti-calmodulin as the solid support. Further couplings embodied in the invention include metal-binding domains for binding histidine-tags, or binders targeting other binders e.g. antibodies bound to other antibodies or antibody-binders like Protein A/G.

In certain non-limiting embodiments, various formats are used to attach the capture tags to a bead, or other solid support. Several embodiments for coupling include, but are not limited to 1) the capture tag attaches to beads present in the droplet library; 2) the capture tag attaches to beads present in sample droplets; 3) the capture tag attaches to beads after release of the combined droplet contents; and 4) the capture tag attaches on a well plate after release of the combined droplet contents.

In some embodiments of the invention, the target analyte sandwich is isolated from the unbound sample components without the use of capture tags or immobilization to a stable support. Such embodiments include but are not limited to using magnetic energy, chemical reactions, pressurized separation with shear stress, or any other system capable of isolating target analyte sandwiches with specificity to allow for analyzing only the target analyte. The preferred embodiment of the invention utilizes capture molecules having capture tags for binding to a stable support.

The support may be a bead that is present in the droplet or it may be a support outside of the droplet. Supports for use in the invention can be two- or three-dimensional and can comprise a planar surface (e.g., a glass slide) or can be shaped. A support substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, composites, or other materials.

Suitable three-dimensional supports include, for example, spheres, microparticles, beads, membranes, slides, plates, micromachined chips, tubes (e.g., capillary tubes), microwells, microfluidic devices, channels, filters, or any other structure suitable for anchoring the capture-tagged binder. Supports can include planar arrays or matrices capable of having regions that include populations of nucleic acids, peptides, sugars, or other molecules. Examples include nucleoside-derivatized CPG and polystyrene slides; derivatized magnetic slides; polystyrene grafted with polyethylene glycol, and the like.

Once the immobilization step occurs such that the sandwich is bound to the solid support, a wash step is performed to isolate sandwich complexes bound to the solid support from remaining components in the sample. In one embodiment, a wash buffer may have sufficient stringency to remove the unincorporated binders and unincorporated non-specific analytes without disrupting the sandwich. In certain embodiments, the wash may just impose a shear stress to remove unwanted and unattached sample and binding elements, however a wash containing binding elements specific to the unwanted sample may increase specificity in the target analyte analysis.

Target Identifier and Sample Identifier Molecules

Generally, the first binding agent, also called the 'barcoded binder', includes an identifier molecule, i.e., a target identifier. The target identifier molecule may be any molecule that is differentially detectable by any detection techniques known in the art. Exemplary detection methods include radioactive detection, optical absorbance detection, e.g., UV-visible absorbance detection, optical emission detection, e.g., fluorescence; phosphorescence or chemiluminescence; Raman scattering, magnetic detection, or mass spectral detection. In certain embodiments, the identifier is an optically detectable label, such as a fluorescent label. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Fluorescently labeled nucleotides may be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739,044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

In other embodiments, the target identifier is a sequence of oligonucleotides that constitutes a unique identifier, or barcode. Attaching barcode sequences to other molecules, such as nucleic acids, is shown for example in Kahvejian et al. (U.S. patent application number 2008/0081330), and Steinman et al. (International patent application number PCT/US09/64001), the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. In certain embodiments, a single barcode is attached to each identifier. In other embodiments, a plurality of barcodes, e.g., two barcodes, are attached to each identifier.

In certain embodiments, the barcode identifier can include features that make it useful in nucleic acid sequencing reactions. For example the barcode sequences are designed to have minimal or no homopolymer regions, i.e., 2 or more of the same base in a row such as AA or CCC, within the barcode sequence.

Methods of designing sets of nucleic acid barcode sequences is shown for example in Brenner et al. (U.S. Pat. No. 6,235,475), the contents of which are incorporated by reference herein in their entirety. In certain non-limiting embodiments, the barcode sequences range from about 4 nucleotides to about 25 nucleotides. In a particular embodiment, the barcode sequences range from about 4 nucleotides to about 7 nucleotides.

When the first binding agent is a nucleic acid, the barcode sequence can be attached to the nucleic acid with an enzyme, or the entire nucleic acid can be synthesised. The enzyme may be a ligase or a polymerase. The ligase may be any enzyme capable of ligating an oligonucleotide (RNA or DNA) to the nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Photo-ligation, chemical attachment, or other methods may also be used to attach the barcode sequence to the nucleic acid-based binder. Non-covalent attachment methods may also be used. One embodiment uses hybridization of complimentary oligonucleotides, between a nucleic acid covalently attached to the first binding agent and an oligonucleotide containing a target identifier.

The target identifier may be coupled to the first binding agent in a releasable manner, such that the identifier may be separated from the first binding agent for purposes of detection in certain embodiments. Alternatively, the target identifier is irreversibly coupled to the first binding agent and detection of the identifier occurs on the complex with the analyte.

In one embodiment for attachment, a modified terminal oligonucleotide is incorporated to the end of an oligonucleotide-encoded identifier. The incorporation may include attaching a UV photo-cleavable primary amino group onto the 5' end of the oligonucleotide binding agent, and subsequently directly attaching the identifier to a protein based binding agent via the amino group. In another embodiment, a UV photo-cleavable oligonucleotide is incorporated into a nucleic acid based binding agent.

Further attachment strategies involve using a bi-functional cross-linking reagent to directly attach an amino acid containing binding agent to an oligonucleotide-based identifier. Embodiments of the method include indirect method attachments, including but not limited to, hybridizing, or annealing, an oligonucleotide identifier to a complimentary oligonucleotide that is either linked to a protein-based binding agent, or incorporated in the sequence of a nucleic acid-based binding agents. Other formats or combinations of the above may also be included, such as attaching a biotinylated or desthiotinylated barcoded oligonucleotide bound to a streptavidin-modified binding agent; attaching DIG, dye, or biotinylated identifying oligonucleotide bound to an antibody to the same motifs bound to the binding agent; and other dimerization motifs, including protein-based nucleic acid-based, or chemical based. Other attachment strategies may be used for protein, nucleic acid, or non-protein or non-nucleic acid binding agents (e.g. chemical modification of lipids, sugars, or synthetic small molecules).

Methods of the invention provide for releasing identifiers isolated after the unbound sample components are removed in the wash. The identifier may be released from the target analyte sandwich using a variety of methods including but not limited to 1) Light-induced release, for example UV-induced photocleavage; 2) Enzymatic release, for example restriction endonuclease, exonuclease, protease; 3) Chemical induced release, for example. metal-catalyzed oxidation; 4) Temperature-induced release, for example release of annealed oligonucleotide; and 5) combinations of the above releasing methods.

Figure 5A:
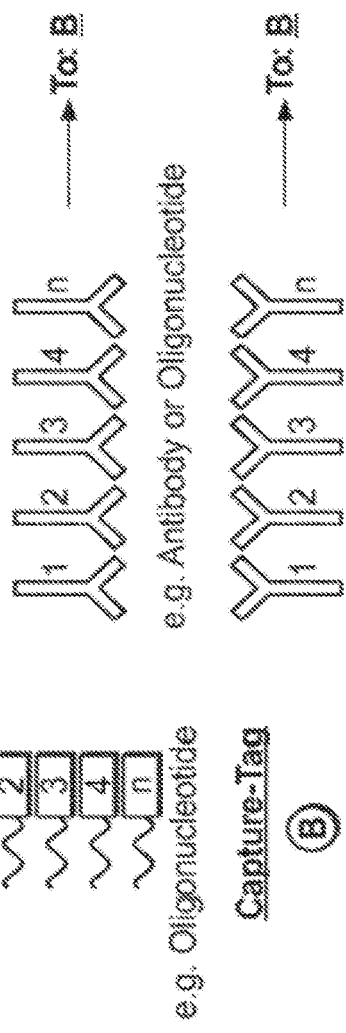
FIG. 5A-FIG. 5B are a schematic illustrating an embodiment of the invention for preparing, attaching, and releasing identifiers for analyzing target analytes.
Figure 5A:
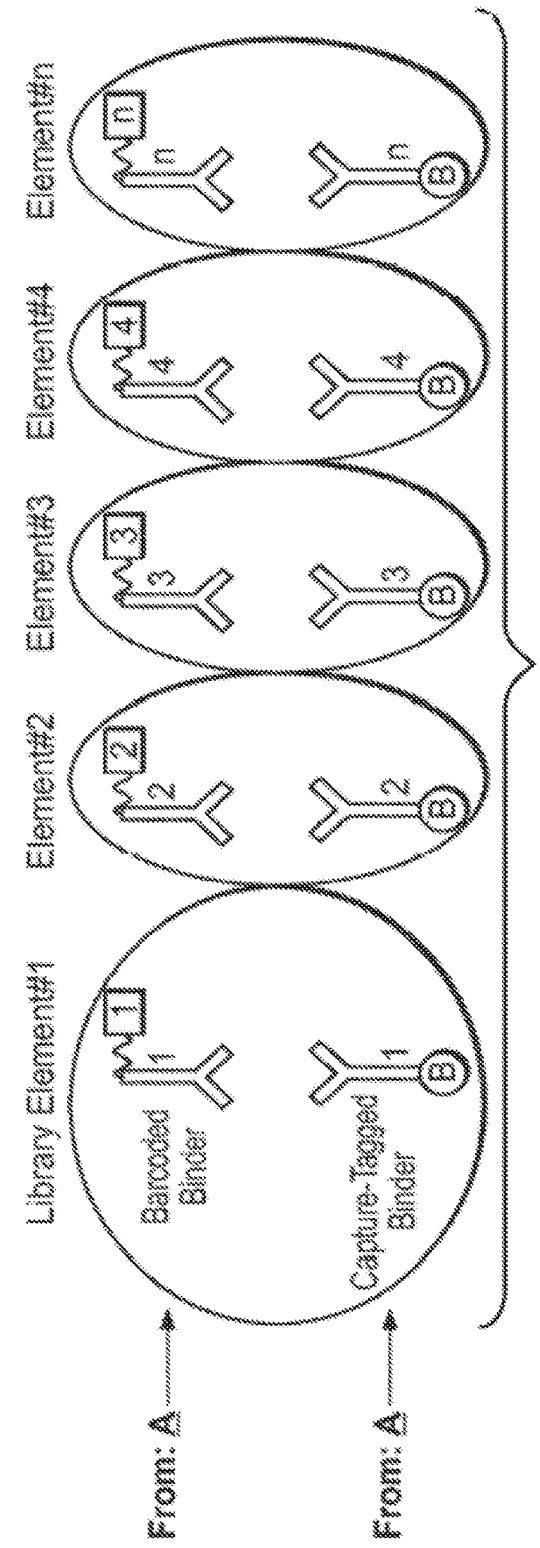
Figure 5B:
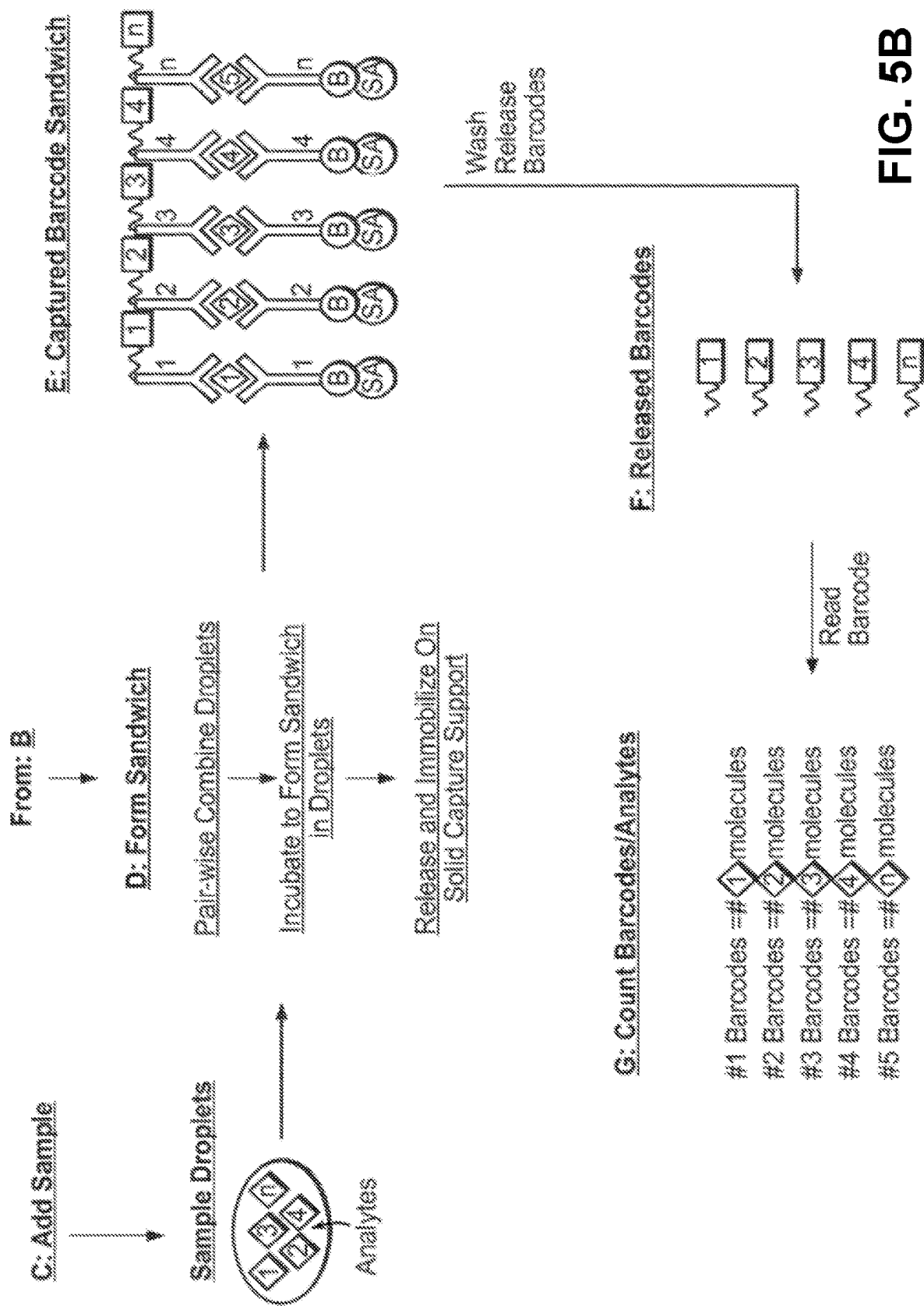
Figure 6D:
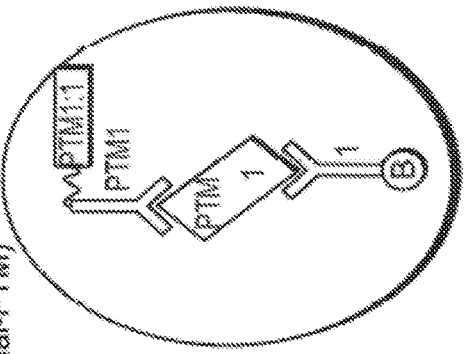
Figure 6H:
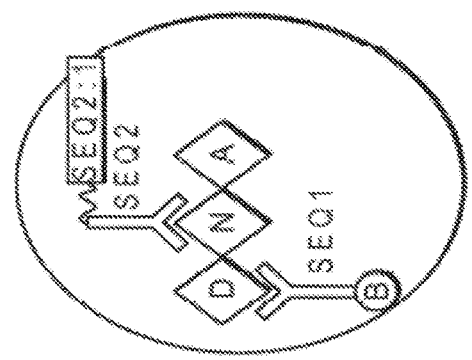
Figure 6C:
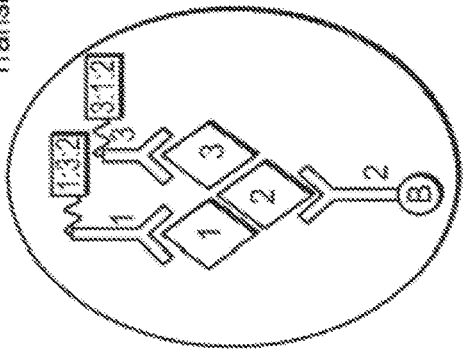
Figure 6G:
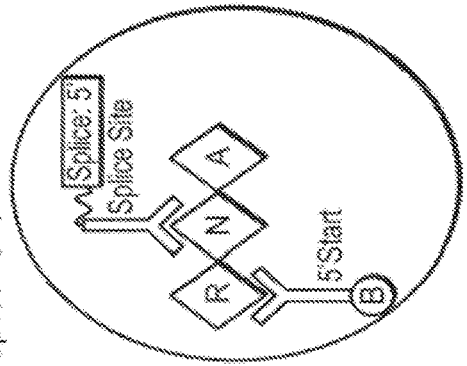
Figure 6B:
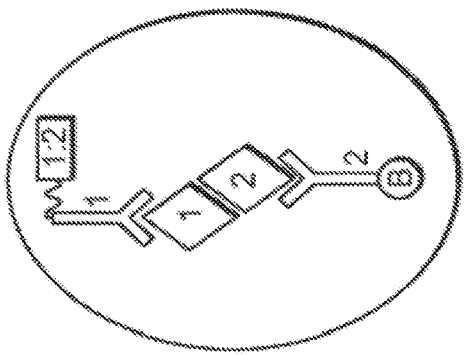
Figure 6F:
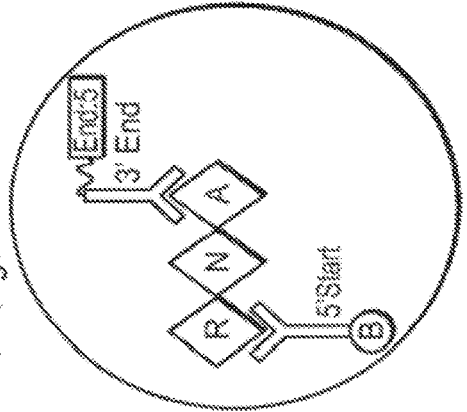
Figure 6A:
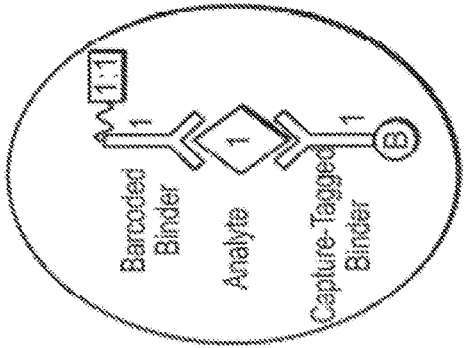
Figure 6E:
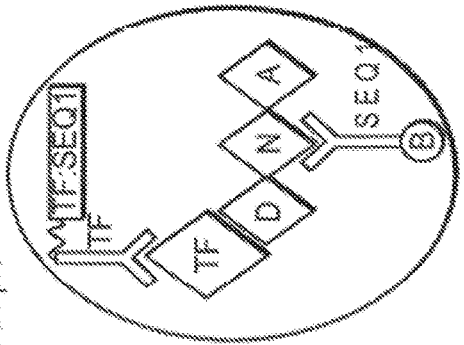

Methods of the invention provide for a capture-tagged binding molecule to correspond with the binding agent having the target identifier, as they are co-encapsulated first in the droplet library element, and subsequently after combination with a sample droplet. The capture molecule and binding agent are considered partner pairs because both are specific to a target analyte and will create a sandwich assay in the presence of the analyte. The barcode identifiers are designed such that each barcode is directly correlated to a particular set of binding agents that are placed together in a single droplet library element for binding a particular target analyte. This allows barcode reads to be correlated back to the binding agents, and thus the target analyte for quantification. Examples of this encoding strategy are shown in FIGS. 5A-B and 6A-J. In FIGS. 5A-B, A) Two binding reagents types are constructed: Barcoded Binders and Capture-Tag Binders; B) Pairs of target-specific binders are made into a droplet library, with each set of target binders in separate droplets; C) The sample is made into sample droplets, and D) combined with the library droplets to initiate highly parallel 'single-plex' binding reactions. After binding is complete, productive sandwiches are E) captured via the capture-tag (streptavidin (SA) biotin (B) interaction shown), and washed to remove unbound material; F) The captured barcodes are released, recovered, and processed for reading; G) Reads for each barcode are counted (e.g. using sequencing). In FIG. 6A, A binder pair targeting two different regions of the same analyte enable counting single target analytes; FIG. 6B & FIG. 6C), Binder pairs targeting different analytes in a complex enable identification and digital quantification of analyte complexes; FIG. 6D) A binder pair targeting two different regions of the same analyte, with one target being a specific modification (e.g. protein post-translational); FIG. 6E) Cross-linked or stable complexes can be analyzed (e.g. protein-nucleic acid); FIGS. 6F-J) Identification and counting of various nucleic acid molecules and motifs are shown (detailed descriptions in the text). Note that the Binder Barcode information includes details on which binders are in the library droplet (e.g. "3:1:2" in example C means Binder3 in the same droplet as Binder1 and Capture-Tag Binder2). In some embodiments of the invention, the capture molecule may have its own or similar identifier to the corresponding identifier attached to the binding agent to use for quantification. In one embodiment, the control identifiers are read after a separate release step.

Figure 8A:
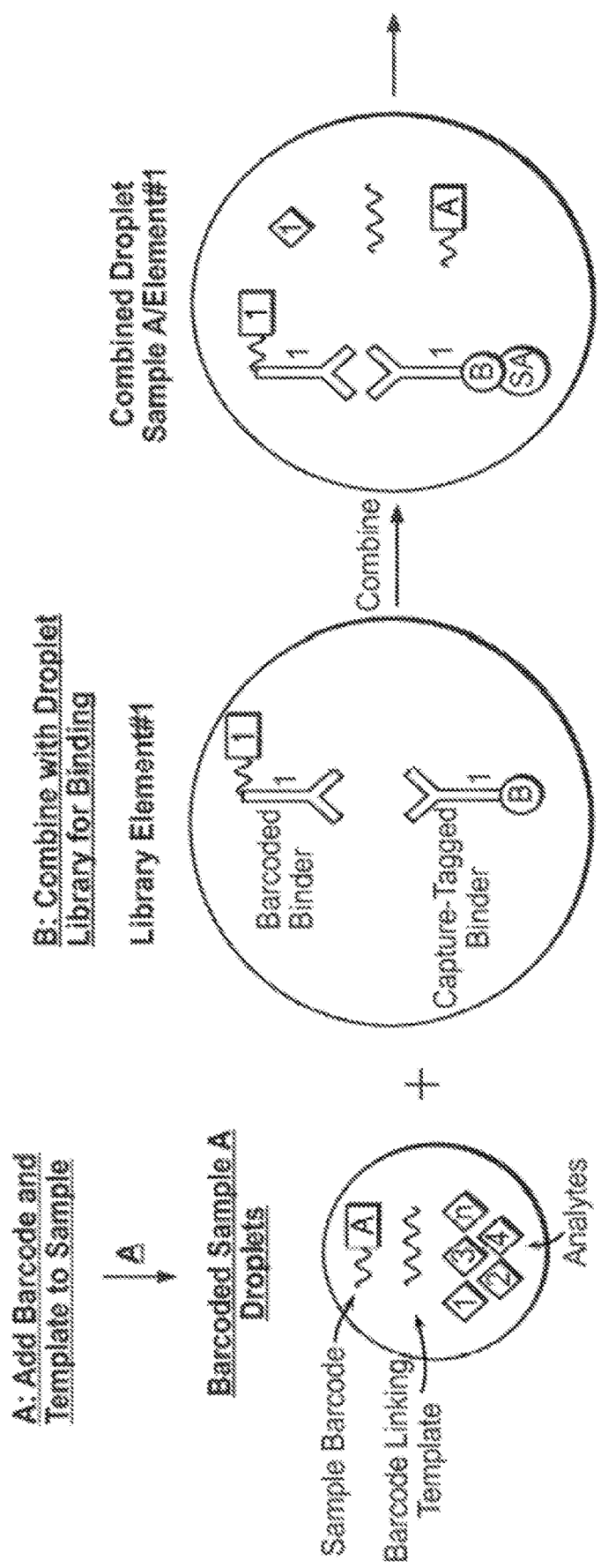
FIG. 8A-FIG. 8B depict introducing a sample identifier to a target analyte identifier in one embodiment of the invention.
Figure 8B:
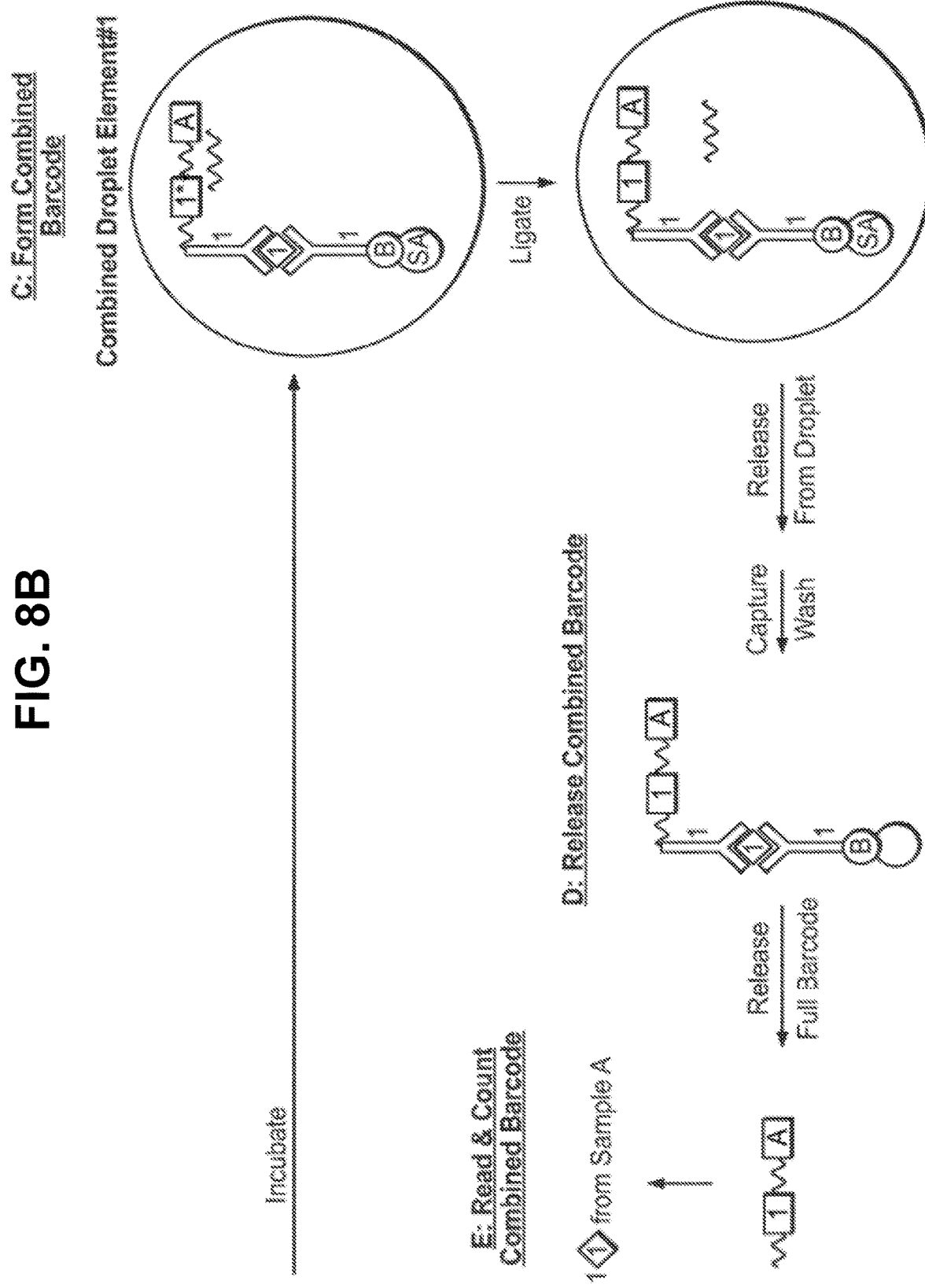
Figure 9A:
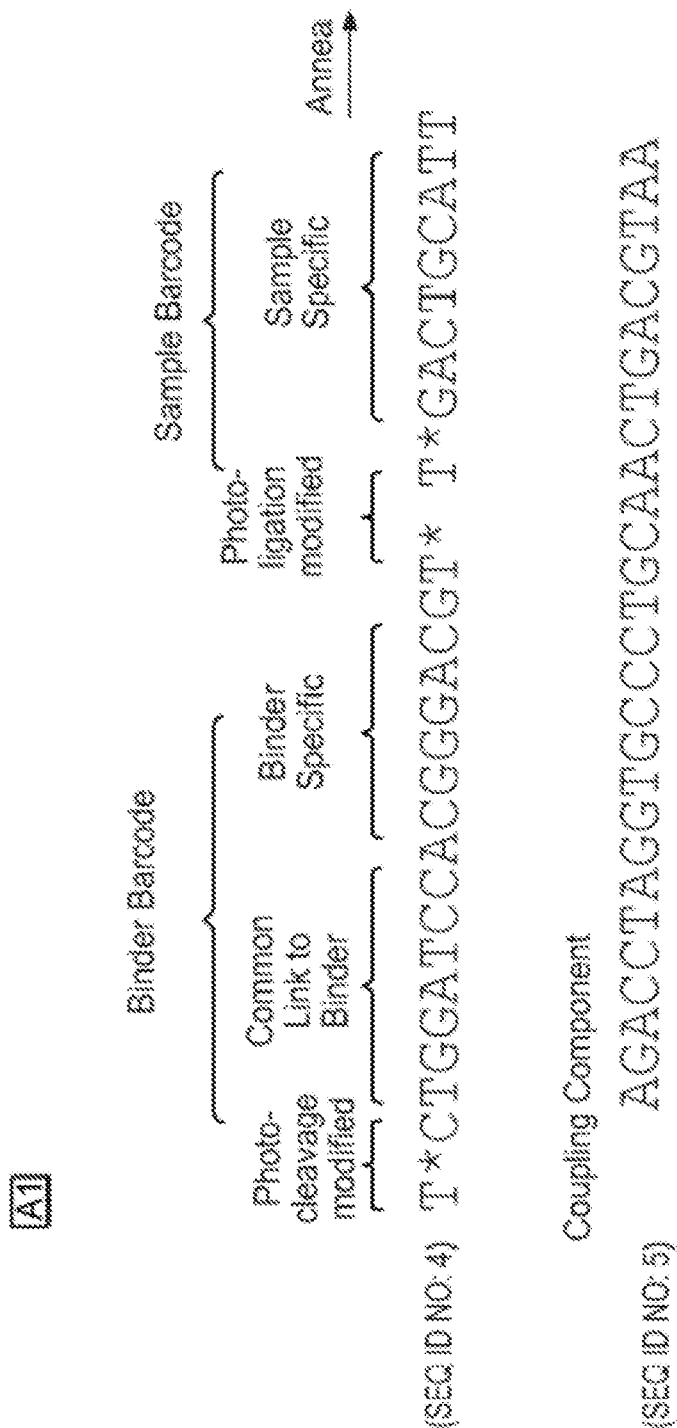
FIG. 9A through FIG. 9C and FIG. 10A through FIG. 10C depict binding of a sample identifier to a target analyte identifier in one embodiment of the invention.
Figure 9B:
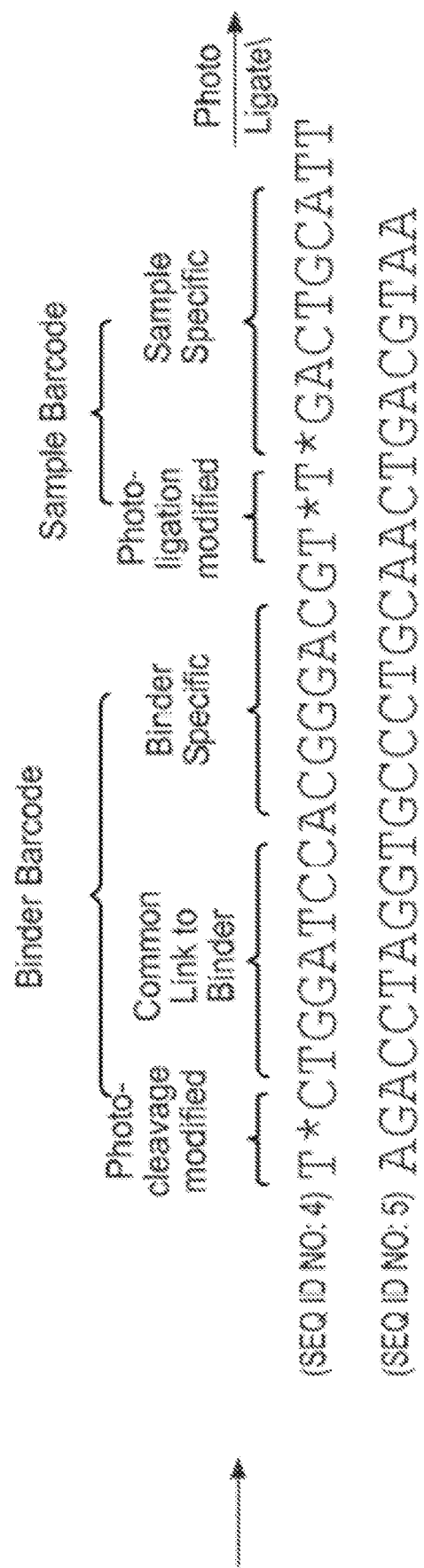
Figure 9C:
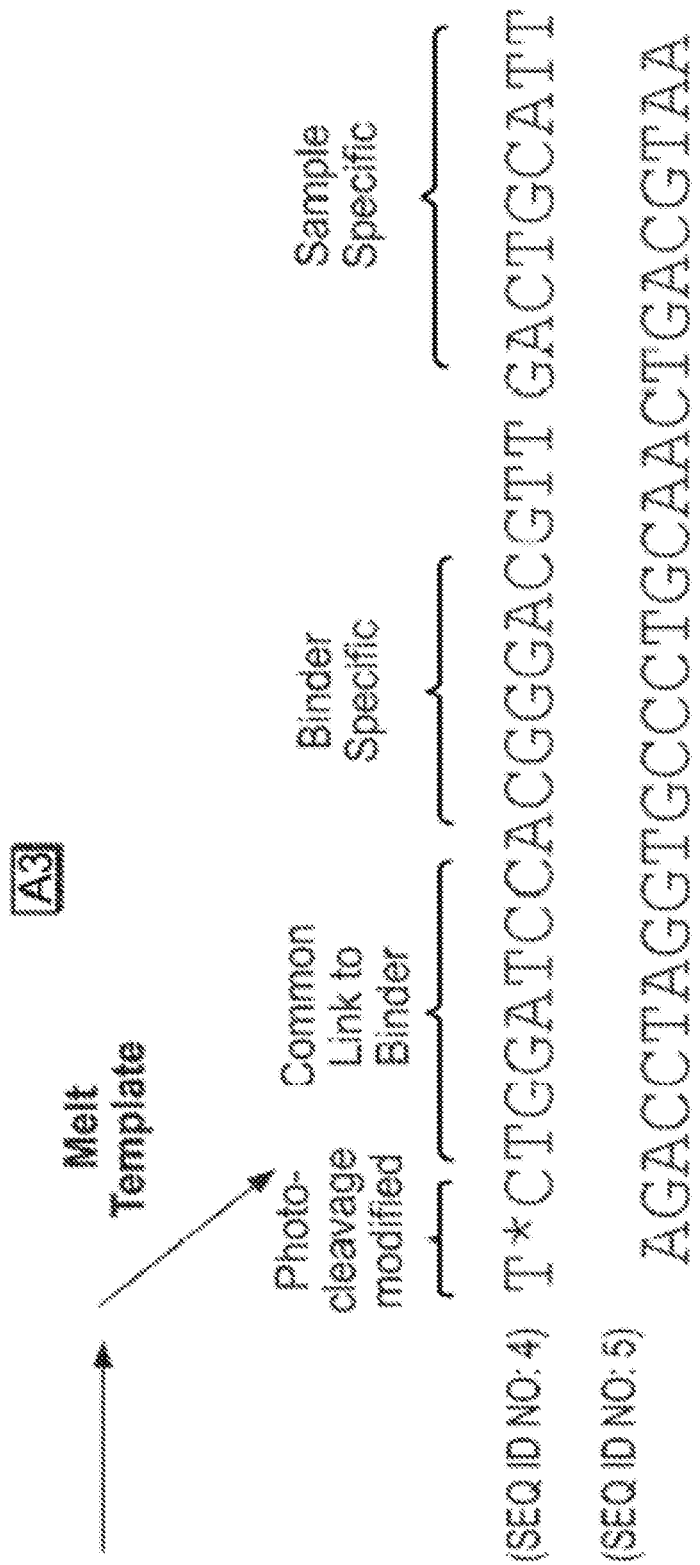
Figure 10A:
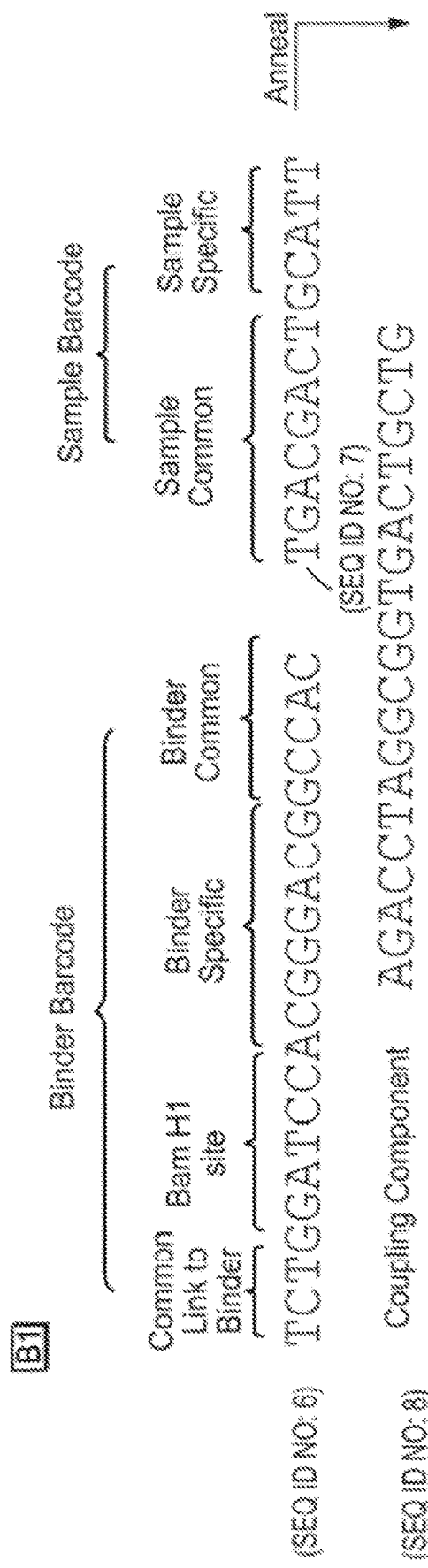
Figure 10B:
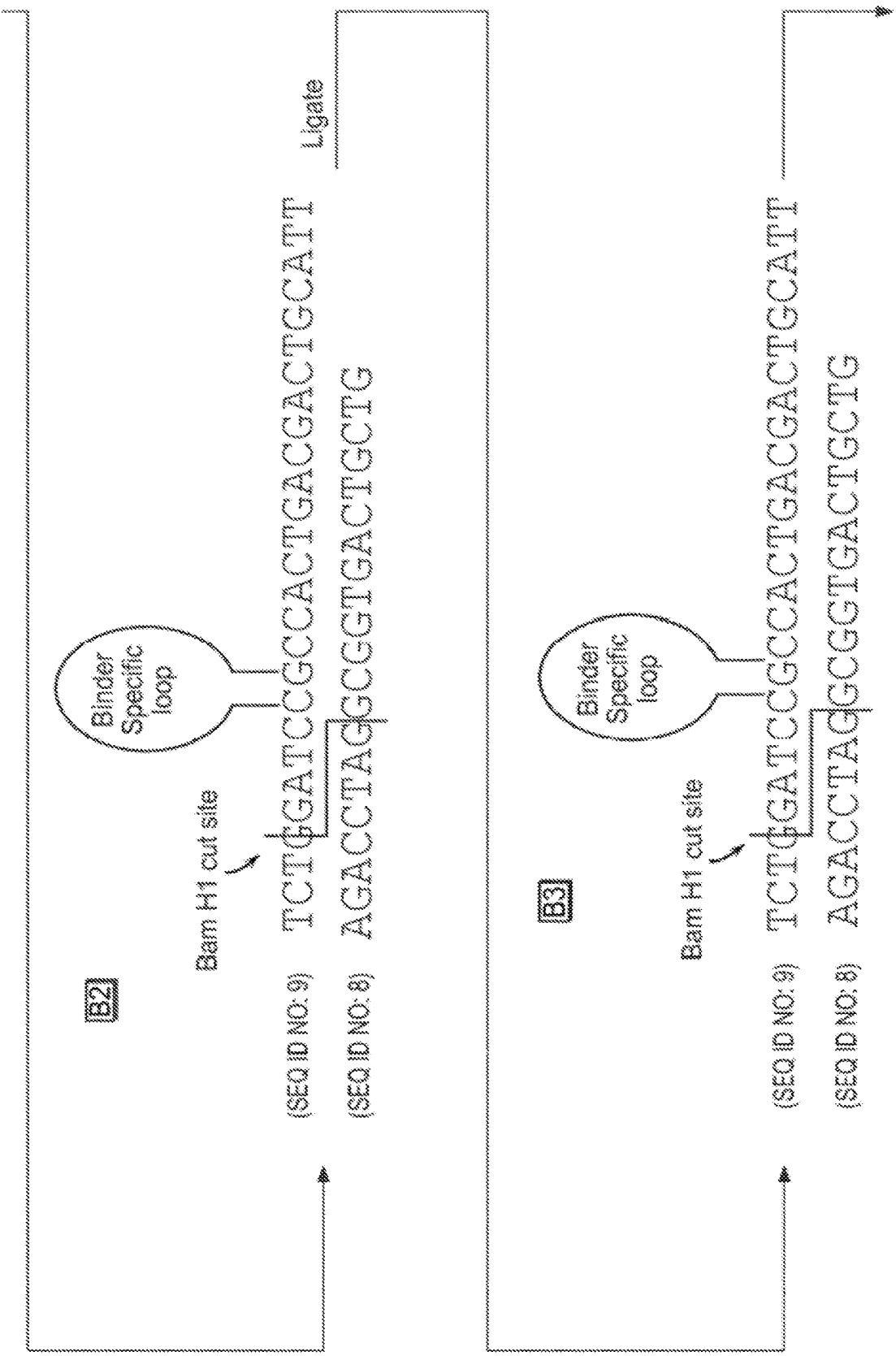
Figure 10C:
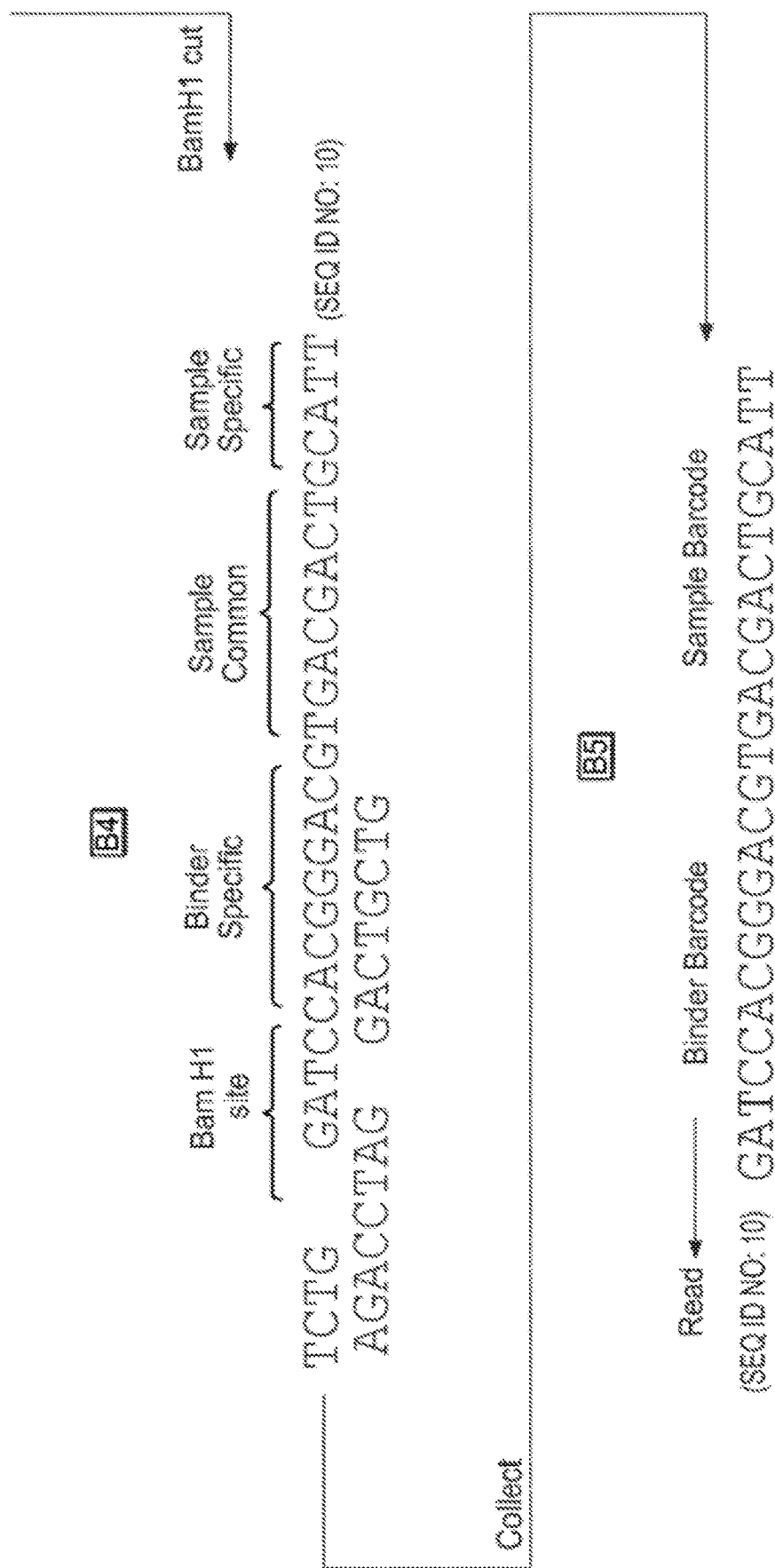

Another method of the invention provides for creating a sample identifier to provide more coding information. In one embodiment, the sample identifier contains information towards identifying that the target analyte came from a certain sample, but sample identifier information may be any extra information useful in analyzing the target analyte. The sample identifier is linked to the target analyte identifier, when the sample and library droplet are combined. One embodiment includes a sample identifier and an identifier linking component within a sample droplet, or the sample linking component can be introduced along with the library droplet, or added in a subsequent step (e.g. another combination or addition to the combined sample and library droplet). In one embodiment, the sample droplet is merged with a library droplet containing a first binding agent having a target analyte identifier and a capture-tagged molecule. When the droplets are merged, a sandwich of the target analyte, first binding agent, and capture-tagged molecule is formed and the sample identifier litigates with the target analyte identifier. In certain embodiments the identifier linking component is a stabilizing molecule to facilitate the ligation of the sample identifier and the target analyte identifier. In certain embodiments, the identifier linking template is not needed, and litigation of the identifier occurs, for example, from affinity of one identifier to the second identifier followed by a reactive step (e.g. ligase, chemical catalysis, light-induced). The unattached sample components are then removed leaving only the isolated sandwich. The combined sample and target analyte identifier are then used to analyze, identify and quantify the target analyte. FIGS. 8A-B demonstrate an embodiment of the invention for creating sandwich assays in combination with combining a sample barcode identifier to a target analyte barcode identifier. In FIG. 8A) Sample Barcode and the Barcode Linking Template are added to bulk Sample A, then made into droplets; FIG. 8B) Sample and Library droplets are combined and incubated to form a sandwich in the presence of the analyte. The Binder Barcode is coupled to the Sample Barcode (e.g. Binder Barcode terminal modified base (*) is photo-ligated to the 5-prime terminal modified base (*) on the Sample Barcode); D) The droplet contents are released and the full sandwich on the capture surface is washed. The Combined Barcode is released (e.g. photo-release); E) Reads for each barcode are counted (e.g. using sequencing). FIGS. 9A through 9B and FIGS. 10A through 10B depict two embodiments of the invention wherein the Binder Barcode and the Sample Barcode are combined into one barcode for anaylsis. In FIG. 9A, modified oligonucleotides are present in the 5-prime terminus of the Sample Barcode and the 3-prime terminus of theBinder Barcode, such that when they are brought together by the Coupling Component (here a oligonucleotide template) and irradiated with 366 nm wavelength light, a photo-catalyzed reaction forms a covalent coupling (e.g. here using 4-thiothymidine (T*)), thus resulting in a combined sample and target analyte identifier. The Coupling Component is melted off, and the final identifier can be released by a photo-cleavage method (using a shorter wavelength). In FIG. 10A, a ligase is used to combine the two barcodes, with the Coupling Component template to align, followed by release using a restriction enzyme site. In FIG. 10A The Barcode Binder, the Sample Barcode and the Barcode Coupling Component (e.g. template spanning the two barcodes) are in the same droplet and; (FIG. 10B) bind as a complex during incubation. The Barcode Coupling Component is a nucleic acid template that hybridizes to both the 5-prime and 3-prime end of the Binder Barcode (forming a hairpin) and the 5-prime end of the Sample Barcode; (FIG. 10C) The 3-prime end of the Binder Barcode is ligated onto the 5-prime end of the Sample Barcode using a ligase; The annealed 5-prime end of the ligated Combined Barcode encodes a restriction endonuclease site that can be cleaved for release of the Combined Barcode.

Another method of the invention provides for a sample identifier to provide more unique coding information. The sample identifier is introduced into the assay to ligate to the target analyte identifier to provide layered information about the target analyte, for example the target analyte is X-protein and X-protein came from sample-Y. In one embodiment, the sample identifier contains identifying information that the target analyte came from a certain sample. The sample identifier, however, may be coded to contain any extra information useful in analyzing the target analyte.

Detection, Reading and Counting Identifiers

Any detection method can be used that is suitable for the type of label employed. Thus, exemplary detection methods include radioactive detection, optical absorbance detection, e.g., UV-visible absorbance detection, optical emission detection, e.g., fluorescence, chemiluminescence, or phosphorescence, Raman scattering, magnetic detection, or mass spectral detection. For fluorescence labeling, a fluorescence microscope apparatus, such as described in Fodor (U.S. Pat. No. 5,445,934) and Mathies et al. (U.S. Pat. No. 5,091,652), may be used to detect the identifiers. Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. A number of approaches can be used to detect the identifiers. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

According to some embodiments of the invention, after barcoded sandwich complexes have been isolated from the remaining components of the sample, the barcode sequences are released from the first binding agents. In one embodiment, the barcode sequences are joined to each other to produce a single contiguous molecule containing multiple barcodes in series. The individual barcodes, collections of separate barcodes, or individual or collections of multiple barcodes connected in series or other arrangements can be detected with or without amplification. In one embodiment, the barcode or barcode collections are subjected to an amplification reaction (e.g., PCR or rolling circle amplification) to produce multiple linear copies (concatamers), linked end-to-end. The amplification products are then sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into an instrument, e.g., HeliScope.™. sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslavsky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLID technology (Applied Biosystems). In SOLID sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton (H+), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods.

Single-Plex Assay Vs. Multi-Plex Assays

All of the previous and following embodiments can be performed as either 'single-plex' or 'multi-plex' assays.

In one embodiment, a combined droplet is formed to allow "single-plex" binding to take place between target analyte and a first binding agent and a capture molecule. The single-plex binding interaction avoids any cross-reactivity which may be found when multiple binding agents are mixed together and may correspond to similar target analytes. FIGS. 5A-B depict creation of single-plex assay. In FIGS. 5A-B: A) Two binding reagents types are constructed: Barcoded Binders and Capture-Tag Binders; B) Pairs of target-specific binders are made into a droplet library (with 'n' elements), with each set of target binders in separate droplets; C) The sample is made into sample droplets, and D) combined with the library droplets to initiate highly parallel 'single-plex' binding reactions. After binding is complete, productive sandwiches are E) captured via the capture-tag (streptavidin (SA) biotin (B) interaction shown), and washed to remove unbound material; F) The captured barcodes are released, recovered, and processed for reading; G) Reads for each barcode are counted (e.g. using sequencing). Another embodiment allows for multi-plex interaction within merged droplet. In order to create multi-plex assays, the first binding agent and second binding agents along with their target analyte have been tested and shown not to cross-react with a second, third, or N-number binding agents and the corresponding second, third or N-number target analytes during sandwich formation. In such embodiment, multiple binding agents are within a droplet library and merged with a sample droplet, wherein multiple target analyte sandwiches are formed with the same specificity as if the combining were performed as a single-plex assay.

In another exemplifying embodiment, a combined droplet is formed to allow "multi-plex" binding to take place between multiple target analytes and multiple first binding agents and multiple capture molecules, i.e. multiple second binding agents with binding pairs. A sample droplet contains a first, second, . . . , N-number target analytes. A droplet library contains a first, second, . . . , N-number first binding agents having an identifier that correspond to a first, second, . . . , N-number second binding agents. The droplets merge to create a first target analyte sandwich, a second target analyte sandwich, . . . , a N-number target analyte sandwich. After immobilization, the unbound sample is washed away, leaving multiple sandwich assays. The barcodes of all the assays are released and processed allowing for complex sample analysis.

In one embodiment, the methods previously described are used for quantification of individual proteins from homogenous liquids, including but not limited to bodily fluids, cell and tissue lystates, and biochemical fractions. Within an embodiment, the amount of a target protein within a sample is determined using a binding agent with an identifier and a capture molecule specific to different regions on a target protein. The target protein specific identifier and capture molecules represent a binding pair. The binding agent with the identifier and the capture molecule attached to different epitopes on the target protein, thus creating a sandwich complex. The identifier contains indentifying information about specific protein, and in one embodiment the identifier a barcode. The identifier may also contain information about the paired capture molecule. Targeting two separate regions with binding pairs increases specificity of the sample. The capture molecule is immobilized to a solid support. After immobilization, the sample is stringently washed removing unattached sample, identifiers, and capture molecules. The remaining sandwich complexes highly correlate with the amount of targeted protein within the sample. An embodiment of the invention provides for releasing the identifier from the sample, for example releasing a barcode by UV photocleavage. The identifier is then counted using sequencing after ligation with NextGen sequencing adapters and sequencing primers. Other methods of ligation may be applied to the identifier to prepare for sequencing. An example of a single target analyte sandwich is shown in FIG. 6A. The above method is not limited to single target proteins and allows for quantification of any single target analyte.

Another embodiment provides for quantification of protein complexes. Protein complexes includes any combination of two or more polypeptide chains, for example epidermal growth factor receptor dimers, a ribosome, a proteasome, a transcription activation pre-initiation complex. Utilizing the sandwich assay method previously described, the protein complex may be identified and counted using identifiers, in certain embodiments the identifiers include barcodes. In one embodiment, a droplet containing a targeted protein complex merged with a library droplet containing a capture molecule specific a first protein complex member and a corresponding binding agent with an identifier specific to second first complex member suspected in the target protein complex. A sandwich is formed wherein the capture molecule is bound to the first protein complex member and the identifier is bound to a second protein complex member. The attached capture molecule then immobilizes the sandwich to a solid substrate, allowing for a stringent wash to remove all unbound sample, identifiers and capture molecules. The remaining sandwiches highly correlate to the amount of targeted protein complexes within the sample. The identifier is released. In one embodiment a barcode attached to the identifier is released using UV photocleavage. Once released, the barcode undergoes ligation with NextGen sequencing adapters and sequencing primers, or other suitable ligation techniques, and then counted using sequencing. An example of a complex sandwich assay is shown in FIG. 6B. The above method is not limited to protein complexes and allows for quantification of any complex analyte containing more than one member.

In a further embodiment, complexes may also be identified and counted using methods of the invention described above. Identifiers specific to complex members can contain identifying information about the target complex member to which they attach (i.e. binder information), but also can contain identifying information relating to the capture molecule or additional binders present in the library droplet. Therefore, the first identifier contains identifying information about the second complex member and the capture molecule, and the second identifier contains identifying information about a third protein complex member and the capture molecule. An example of a complex analyte sandwich is shown in FIG. 6C (e.g. "3:1:2" in example C means Binder3 in the same droplet as Binder1 and Capture-Tag Binder2).

In another embodiment, quantification of post-translational modifications from homogenous liquids including bodily fluids, cell and tissue lysates, and biochemical fractions. Post-translational modifications of proteins include phosphorylation, methylation, glycosylation, and ubiquitinylation and are critical components of protein function. Methods of the invention allow for identifying and quantifying specific post-translational modification proteins within a sample. In one embodiment a binding agent is specific to a invariant epitope and the other biding agent is specific to a sequence-specific post-translational modification. In one embodiment, a first binding agent with an identifier, in one embodiment a barcode, is specific to an invariant epitope on the target protein, and a capture molecule is specific to sequence-specific post-translational modification. When introduced to the target protein, the target protein forms a sandwich with the first binding agent and the capture molecule. The sandwich is separated from unattached samples and binding agents, wherein separation may occur from immobilization followed by a stringent wash. The remaining sandwiches highly correlate to the amount of target proteins having the post-translational modification. In one embodiment, the identifier is released from the sandwich by a UV photocleavage and the identifier is then used to analyze the target protein. In one embodiment, the barcode is ligated using NextGen sequencing adapters and sequencing primers and then analyzes the target protein via sequencing. Example of a single sandwich wherein the target analyte is a post-translation modification is illustrated on FIG. 6D.

Modifications that can be detected using the above methods are not limited to post-translational protein modifications, but apply to any modification for which a specific binding agent is available.

Methods of the invention also provide for quantification of individual nucleic acids from homogenous liquids (liquids including bodily fluids, cell and tissue lysate, and biochemical fractions). In one embodiment, a specific region on a nucleic may be detected using methods of the invention. A first binding agent is specific to a first region on the nucleic acid, and a second binding agent specific to the second region on the nucleic acid. The first or the second binding agent may comprise a capture molecule or having an identifier. When the first and second binding agents attach to the corresponding regions on the target region and a sandwich is produced. In one embodiment, a sandwich is created for SNP detection of DNA wherein the capture molecule is specific to a target wild type sequence nearby the potential SNP-containing sequence and the binding agent having a identifier is specific to potential SNP (see FIG. 6H). In another embodiment, a gene fusion is detected wherein the capture molecule is specific to target sequences nearby the potential fusion junction on gene 1 and the binding agent having a identifier is specific to sequences found on gene 2 when fused to gene 1 (see FIG. 6I). In another embodiment, full-length mRNA is detected wherein the capture molecule is specific to the transcriptional start sequence region and the identifier is specific to the 3-prme end region (See FIG. 6F). In another embodiment, splice variants are detected wherein a capture molecule is specific to the transcriptional start sequence region and the binding agent is specific to the splice variant region (see FIG. 6G). In another embodiment, modified DNA (e.g., methylation or hydroxyl-methylation of cytosine) is detected using a capture molecule specific to a nearby DNA motif and a barcoded binding agent specific for modified DNA sequences. Other embodiments of the invention includes detecting untranslated RNA (including miRNA or lincRNA), and binding complexes of DNA to DNA, DNA to RNA, DNA or RNA to protein (see FIG. 6E). In a further embodiment, introduction of a competitive inhibitor increases specificity to ensure the binding agent or capture molecule are not binding on unspecific target regions (similar to the example in FIG. 7).

Embodiments of the invention further include using sandwich assays in droplets for quantification of proteins, nucleic acids, and other molecules from single cells. An embodiment of the invention provides for encapsulating a series of single cell containing droplets by using collections of single cells dispersed in liquid, for example a growth media or a phosphate buffered saline for droplet creation similar to methods described above. In order to create droplets containing only single cells, the concentration of single cells in a collection is diluted to minimize multiple cell encapsulation. One embodiment of the invention dilutes the single cell concentration to a level where only one cell is present for every 10 droplets formed. Once single cell droplets are formed, they are incubated in order to allow secreted molecules of interest to accumulate inside the droplet, one can lyse the cell using reagents that release the cellular nucleic acids, proteins, and other components from cell compartments, or one can use immediately to analyze cell surface exposed material, or one can combine these various analysis schemes. Each single cell droplet is combined with a library droplet in which a variety of assays may be conducted using methods of the invention including 1) analysis of secreted molecules including but not limited to cytokines and growth factors by combining viable single cells with a first binding agent and a second binding agent specific to target secreted molecules; 2) analysis of cell surface molecules including but not limited to receptors and biomarkers by combining a single cell with a droplet library containing a first binding agent and a second binding agent specific to target molecules; 3) analysis of molecules released from single cells lysed inside droplets including but not limited to cytoplasmic or nuclear proteins by combining lysed single cell droplets with a first binding agent and a second binding agent specific to a target intracellular molecule; 4) any combination of the above assays.

Methods of the invention further provide for conducting further assays previously described for use with single cell droplets, including quantification of individual proteins, protein post-translational modifications, protein complexes, protein/DNA complexes, and nucleic acids. In further embodiments, a combination of assays may be performed. In a non-limiting example, an assay may be performed by targeting both secreted molecules and cell surface molecules from the same cell. In another non-limiting example, a secreted target can be assayed before cell lysis is induced, followed by cell lysis within the droplet and subsequently assaying an intracellular target using additional binding and capture agents in the library element, or by subsequent combination with a second library element droplet. Typical, but non-limiting methods for cell lysis within droplets include: 1) co-flowing a lysis buffer in a laminar flow alongside the incoming cell stream in the flow path just before the droplet-forming microfluidic nozzle; 2) introducing a lysis buffer within the droplet library reagents; 3) use of a temperature or other inducible protease or lysis reagent; 4) mechanical abrasion inside droplets traveling through microfluidic turns and constrictions; 5) laser-induced lysis. Library droplets used for single cell analysis can contain paired binders for single-target analysis, or multiple binding pairs for multi-plex target analysis (as long as the multiple binding pairs retain sufficient specificity when in the same compartment). In a preferred embodiment, the single cell droplet contains a sample identifier and all individual molecule droplets dependent from the sample also have the same sample identifier. Therefore, the sample identifier combines with the target analyte identifier so all sandwiches can be traced to the sample.

In another embodiment, target analyte sandwiches are run on bulk samples without the need for droplets, if cross reactivity or specificity of binding pairs in the presence of other binding pairs is not an issue. In such embodiment, a identifier library is created to analyze the target analytes within the sample without the use of droplets, and all related steps needed for quantifying the analytes with use of barcodes also do not require droplets, i.e. capture occurs on beads in a bulk solution instead of in a droplet.

Libraries and Kits

Droplet libraries are useful to perform large numbers of assays while consuming only limited amounts of reagents. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. As used herein, a first entity is "surrounded" by a second entity if a closed loop can be drawn or idealized around the first entity through only the second entity.

In general, a droplet library is made up of a number of library elements that are pooled together in a single collection. Libraries may vary in complexity from a single library element to 1015 library elements or more. Each library element is one or more given components at a fixed concentration. Each droplet includes a first binding agent having a differentially detectable identifier and a second binding agent. The binding agents may be any of the agents described above. Each droplet may further include a sample identifier that can bind to the identifier linked to the first binding agent. In this manner, each droplet includes an identifier for a particular target analyte and an identifier for a specific droplet. Each droplet may further include a competitive inhibitor. The terms "droplet library" or "droplet libraries" are also referred to herein as an "emulsion library" or "emulsion libraries." These terms are used interchangeably throughout the specification.

The droplets range in size from roughly 0.5 micron to 500 micron in diameter, which corresponds to about 1 pico liter to 1 nano liter. However, droplets can be as small as 5 microns and as large as 500 microns, Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention may be uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability can be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

In certain embodiments, the present invention provides an emulsion library comprising a plurality of aqueous droplets within an immiscible fluorocarbon oil comprising at least one fluorosurfactant, wherein each droplet is uniform in size and comprises the same aqueous fluid and comprises a different library element. The present invention also provides a method for forming the emulsion library comprising providing a single aqueous fluid comprising different library elements, encapsulating each library element into an aqueous droplet within an immiscible fluorocarbon oil comprising at least one fluorosurfactant, wherein each droplet is uniform in size and comprises the same aqueous fluid and comprises a different library element, and pooling the aqueous droplets within an immiscible fluorocarbon oil comprising at least one fluorosurfactant, thereby forming an emulsion library.

For example, in one type of emulsion library, the first and second binding agents are pooled in a single source contained in the same medium. After the initial pooling, the first and second binding agents are then encapsulated in droplets to generate a library of droplets wherein each droplet includes a different set of first and second binding agents. The dilution of the initial solution enables the encapsulation process. In some embodiments, the droplets formed will either contain a single set of first and second binding agents or having nothing, i.e., be empty. In other embodiments, the droplets formed will contain multiple sets of first and second binding agents so that multiplexing may be performed in each droplet.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

The invention claimed is:

1. A method comprising:
incubating a target analyte with binding agents, wherein the binding agents comprise binders linked to oligonucleotides,
wherein each binding agent is provided with barcode sequences that include a target analyte identifier and a unique identifier unique to the binding agent;
binding one of the binding agents to the target analyte; and
sequencing the barcode sequences to detect the target analyte.

2. The method of claim 1, wherein the binders are antibodies.

3. The method of claim 1, further comprising releasing the barcode sequences from the binding agent prior to the sequencing step.

4. The method of claim 1, wherein the target analyte is a protein.

5. The method of claim 4, wherein the protein comprises a cell surface protein or a protein secreted by cells.

6. The method of claim 4, wherein the binders are aptamers.

7. The method of claim 1, wherein the target analyte is protein from cells in a sample and the method includes isolating the cells into partitions.

8. The method of claim 7, wherein each barcode sequence further includes an identifier specific for one of the partitions.

9. The method of claim 8, wherein the identifier specific for the partition is detected to associate the detection of the target analyte with the partition.

10. The method of claim 7, further comprising lysing the cells in the partitions.

11. A method comprising:
incubating a target analyte with binding agents, wherein the binding agents comprise antibodies linked to oligonucleotides, wherein the target analyte is a protein;
binding one of the binding agents to the target analyte, wherein each binding agent is provided with barcode sequences that include a target analyte identifier sequence and a unique identifier sequence unique to the binding agent; and
sequencing the barcode sequences to detect the target analyte.

12. The method of claim 11, further comprising releasing the barcode sequences from the binding agent prior to the sequencing step.

13. The method of claim 12, wherein the protein comprises a cell surface protein or a protein secreted by cells.

14. The method of claim 11, wherein the target analyte is protein from cells in a sample and the method includes isolating the cells into partitions.

15. The method of claim 14, wherein each barcode sequence further includes an identifier specific for one of the partitions.

16. The method of claim 15, wherein the identifier specific for the partition is detected to associate the detection of the target analyte with the partition.

17. The method of claim 14, further comprising lysing the cells in the partitions.

* * * * *

```
                            SEQUENCE LISTING

Sequence total quantity: 10
SEQ ID NO: 1            moltype = DNA  length = 15
FEATURE                 Location/Qualifiers
misc_feature            1..15
                        note = Synthetic Sequence
source                  1..15
                        mol_type = other DNA
                        organism = synthetic construct
SEQUENCE: 1
tcgttcgagt cataa                                                          15

SEQ ID NO: 2            moltype = DNA  length = 15
FEATURE                 Location/Qualifiers
misc_feature            1..15
                        note = Synthetic Sequence
source                  1..15
                        mol_type = other DNA
                        organism = synthetic construct
SEQUENCE: 2
tcgttcgagt gataa                                                          15

SEQ ID NO: 3            moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 3
tagttcagtc cgtc                                                           14

SEQ ID NO: 4            moltype = DNA  length = 28
FEATURE                 Location/Qualifiers
misc_feature            1..28
                        note = Synthetic Sequence
source                  1..28
                        mol_type = other DNA
                        organism = synthetic construct
SEQUENCE: 4
tctggatcca cgggacgttg actgcatt                                            28

SEQ ID NO: 5            moltype = DNA  length = 28
FEATURE                 Location/Qualifiers
misc_feature            1..28
                        note = Synthetic Sequence
source                  1..28
                        mol_type = other DNA
                        organism = synthetic construct
SEQUENCE: 5
agacctaggt gccctgcaac tgacgtaa                                            28

SEQ ID NO: 6            moltype = DNA  length = 22
FEATURE                 Location/Qualifiers
misc_feature            1..22
                        note = Synthetic Sequence
source                  1..22
```

```
                        mol_type = other DNA
                        organism = synthetic construct
SEQUENCE: 6
tctggatcca cgggacggcc ac                                                 22

SEQ ID NO: 7            moltype = DNA   length = 13
FEATURE                 Location/Qualifiers
misc_feature            1..13
                        note = Synthetic Sequence
source                  1..13
                        mol_type = other DNA
                        organism = synthetic construct
SEQUENCE: 7
tgacgactgc att                                                           13

SEQ ID NO: 8            moltype = DNA   length = 21
FEATURE                 Location/Qualifiers
misc_feature            1..21
                        note = Synthetic Sequence
source                  1..21
                        mol_type = other DNA
                        organism = synthetic construct
SEQUENCE: 8
agacctaggc ggtgactgct g                                                  21

SEQ ID NO: 9            moltype = DNA   length = 27
FEATURE                 Location/Qualifiers
misc_feature            1..27
                        note = Synthetic Sequence
source                  1..27
                        mol_type = other DNA
                        organism = synthetic construct
SEQUENCE: 9
tctggatccg ccactgacga ctgcatt                                            27

SEQ ID NO: 10           moltype = DNA   length = 26
FEATURE                 Location/Qualifiers
misc_feature            1..26
                        note = Synthetic Sequence
source                  1..26
                        mol_type = other DNA
                        organism = synthetic construct
SEQUENCE: 10
gatccacggg acgtgacgac tgcatt                                             26
```